(12) United States Patent
Lu et al.

(10) Patent No.: US 11,952,402 B2
(45) Date of Patent: Apr. 9, 2024

(54) FUSION PROTEIN CONTAINING TRAIL AND IgG BINDING DOMAIN AND THE USES THEREOF

(71) Applicant: WEST CHINA HOSPITAL, SICHUAN UNIVERSITY, Sichuan (CN)

(72) Inventors: Xiaofeng Lu, Sichuan (CN); Hao Yang, Sichuan (CN); Ze Tao, Sichuan (CN); Jingqiu Cheng, Sichuan (CN)

(73) Assignee: WEST CHINA HOSPITAL, SICHUAN UNIVERSITY, Sichuan (CN)

( * ) Notice: Subject to any disclaimer, the term of this patent is extended or adjusted under 35 U.S.C. 154(b) by 752 days.

(21) Appl. No.: 16/989,654

(22) Filed: Aug. 10, 2020

(65) Prior Publication Data
US 2021/0101944 A1    Apr. 8, 2021

Related U.S. Application Data

(63) Continuation-in-part of application No. PCT/CN2019/073994, filed on Jan. 30, 2019.

(30) Foreign Application Priority Data

Feb. 8, 2018 (CN) .......................... 201810128333.0

(51) Int. Cl.
| | |
|---|---|
| *C07K 14/315* | (2006.01) |
| *A61K 38/16* | (2006.01) |
| *A61K 38/17* | (2006.01) |
| *A61P 35/00* | (2006.01) |
| *C07K 14/705* | (2006.01) |
| *C07K 16/28* | (2006.01) |

(52) U.S. Cl.
CPC .......... *C07K 14/315* (2013.01); *A61K 38/164* (2013.01); *A61K 38/177* (2013.01); *A61P 35/00* (2018.01); *C07K 14/70575* (2013.01); *C07K 16/2803* (2013.01); *C07K 16/2863* (2013.01); *C07K 2319/00* (2013.01)

(58) Field of Classification Search
CPC ............ C07K 2319/00; C07K 2319/31; C07K 2319/70; C07K 14/70575; C07K 14/315; A61K 38/164
See application file for complete search history.

(56) References Cited

U.S. PATENT DOCUMENTS

2004/0254108 A1 * 12/2004 Ma .................. C07K 14/475
514/18.9
2017/0145062 A1    5/2017 Kontermann et al.

FOREIGN PATENT DOCUMENTS

| CN | 106519040 A | 3/2017 | |
|---|---|---|---|
| WO | WO-2006089015 A2 * | 8/2006 | ........... A61K 31/517 |
| WO | WO-2013041730 A1 * | 3/2013 | ....... A61K 39/39591 |
| WO | 2013156054 A1 | 10/2013 | |
| WO | WO-2016011003 A1 * | 1/2016 | ............. A61K 38/00 |

OTHER PUBLICATIONS

Lim et al (Expert Opinion on Therapeutic Targets, 2015, vol. 19, pp. 1171-1185) (Year: 2015).*
Giusti et al (The Oncologist, 2007, vol. 12, pp. 577-583) (Year: 2007).*
Muller et al (Journal of Biological Chemistry, 2007, vol. 282, pp. 12650-12660) (Year: 2007).*
Siegemound, Martin et al.; An optimized antibody-single-chain TRAIL fusion protein for cancer therapy; MABS, vol. 8, No. 5, pp. 879-891, Dec. 31, 2016.
Hakansson, Susanna et al.; Heparin binding by the HIV-1 tat protein transduction domain; Protein Science, vol. 10, pp. 2138-2139, Dec. 31, 2001.
Yang, Hao et al.; Endogenous IgG-based affinity-cntrolled release of TRAIL exerts superior antitumor effects; Theranostics, vol. 8, Issue 9, 2459-2476, Mar. 28, 2018.
Achari, Aniruddha et al.; 1.67-A X-ray Structure of the B2 Immunoglobulin-Binding Domain of Streptococcal Protein G and Comparison to the NMR Structure of the B1 Domain; Biochemistry 1992, vol. 31, No. 43, pp. 10449-10457.

* cited by examiner

*Primary Examiner* — Karen A. Canella
(74) *Attorney, Agent, or Firm* — NKL Law; Allen Xue

(57) ABSTRACT

A recombinant protein includes a TRAIL domain and an IgG binding domain IgBD. In the recombinant protein, IgBD can be fused at the N-terminus or C-terminus of the TRAIL domain. The anti-tumor effect of the recombinant protein after binding to endogenous or exogenous IgG is significantly stronger than that of TRAIL, and can be used in the treatment of cell proliferative diseases with high expression of death receptors.

15 Claims, 18 Drawing Sheets

Specification includes a Sequence Listing.

SEQUENCE LISTING

<160> NUMBER OF SEQ ID NOS: 28

<210> SEQ ID NO 1
<211> LENGTH: 168
<212> TYPE: PRT
<213> ORGANISM: Homo sapiens
<220> FEATURE:
<221> NAME/KEY: misc_feature
<223> OTHER INFORMATION: TRAIL 01

<400> SEQUENCE: 1

Val Arg Glu Arg Gly Pro Gln Arg Val Ala Ala His Ile Thr Gly Thr
1               5                   10                  15

Arg Gly Arg Ser Asn Thr Leu Ser Ser Pro Asn Ser Lys Asn Glu Lys
            20                  25                  30

Ala Leu Gly Arg Lys Ile Asn Ser Trp Glu Ser Ser Arg Ser Gly His
        35                  40                  45

Ser Phe Leu Ser Asn Leu His Leu Arg Asn Gly Glu Leu Val Ile Gln
    50                  55                  60

Glu Lys Gly Phe Tyr Tyr Ile Tyr Ser Gln Thr Tyr Phe Arg Phe Gln
65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Leu Phe Glu Leu Lys Lys Asp Asp Arg Ile Phe
    130                 135                 140

Val Ser Val Thr Asn Glu His Leu Ile Asp Met Asp His Glu Ala Ser
145                 150                 155                 160

Phe Phe Gly Ala Phe Leu Val Gly
                165

<210> SEQ ID NO 2
<211> LENGTH: 56
<212> TYPE: PRT
<213> ORGANISM: Homo sapiens
<220> FEATURE:
<221> NAME/KEY: misc_feature
<223> OTHER INFORMATION: IgBD 01

<400> SEQUENCE: 2

Thr Thr Tyr Lys Leu Val Ile Asn Gly Lys Thr Leu Lys Gly Glu Thr
1               5                   10                  15

Thr Thr Lys Ala Val Asp Ala Glu Thr Ala Ala Ala Phe Ala Gln
            20                  25                  30

Tyr Ala Arg Arg Asn Gly Val Asp Gly Val Trp Thr Tyr Asp Asp Ala
        35                  40                  45

Thr Lys Thr Phe Thr Val Thr Glu
    50                  55

<210> SEQ ID NO 3
<211> LENGTH: 56
<212> TYPE: PRT
<213> ORGANISM: Homo sapiens
<220> FEATURE:
<221> NAME/KEY: misc_feature
<223> OTHER INFORMATION: IgBD 02

<400> SEQUENCE: 3

Thr Thr Tyr Lys Leu Val Ile Asn Gly Lys Thr Leu Lys Gly Glu Thr
1               5                   10                  15

Thr Thr Lys Ala Val Asp Ala Glu Thr Ala Glu Lys Ala Phe Lys Gln
                20                  25                  30

Tyr Ala Asn Asp Asn Gly Val Asp Gly Val Trp Thr Tyr Asp Asp Ala
            35                  40                  45

Thr Lys Thr Phe Thr Val Thr Glu
        50                  55

<210> SEQ ID NO 4
<211> LENGTH: 15
<212> TYPE: PRT
<213> ORGANISM: Homo sapiens
<220> FEATURE:
<221> NAME/KEY: misc_feature
<223> OTHER INFORMATION: (G4S)3

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 239
<212> TYPE: PRT
<213> ORGANISM: Homo sapiens
<220> FEATURE:
<221> NAME/KEY: misc_feature
<223> OTHER INFORMATION: IgBD-TRAIL01

<400> SEQUENCE: 5

Thr Thr Tyr Lys Leu Val Ile Asn Gly Lys Thr Leu Lys Gly Glu Thr
1               5                   10                  15

Thr Thr Lys Ala Val Asp Ala Glu Thr Ala Ala Ala Phe Ala Gln
                20                  25                  30

Tyr Ala Arg Arg Asn Gly Val Asp Gly Val Trp Thr Tyr Asp Asp Ala
            35                  40                  45

Thr Lys Thr Phe Thr Val Thr Glu Gly Gly Gly Ser Gly Gly Gly
        50                  55                  60

Gly Ser Gly Gly Gly Ser Val Arg Glu Arg Gly Pro Gln Arg Val
65                  70                  75                  80

Ala Ala His Ile Thr Gly Thr Arg Gly Arg Ser Asn Thr Leu Ser Ser
                85                  90                  95

Pro Asn Ser Lys Asn Glu Lys Ala Leu Gly Arg Lys Ile Asn Ser Trp
                100                 105                 110

Glu Ser Ser Arg Ser Gly His Ser Phe Leu Ser Asn Leu His Leu Arg
            115                 120                 125

Asn Gly Glu Leu Val Ile Gln Glu Lys Gly Phe Tyr Tyr Ile Tyr Ser
        130                 135                 140

Gln Thr Tyr Phe Arg Phe Gln Glu Glu Ile Lys Glu Asn Thr Lys Asn
145                 150                 155                 160

Asp Lys Gln Met Val Gln Tyr Ile Tyr Lys Tyr Thr Ser Tyr Pro Asp
                165                 170                 175

Pro Ile Leu Leu Met Lys Ser Ala Arg Asn Ser Cys Trp Ser Lys Asp
            180                 185                 190

Ala Glu Tyr Gly Leu Tyr Ser Ile Tyr Gln Gly Gly Leu Phe Glu Leu
        195                 200                 205

Lys Lys Asp Asp Arg Ile Phe Val Ser Val Thr Asn Glu His Leu Ile
        210                 215                 220

```
Asp Met Asp His Glu Ala Ser Phe Phe Gly Ala Phe Leu Val Gly
225                 230                 235
```

<210> SEQ ID NO 6
<211> LENGTH: 239
<212> TYPE: PRT
<213> ORGANISM: Homo sapiens
<220> FEATURE:
<221> NAME/KEY: misc_feature
<223> OTHER INFORMATION: IgBD-TRAIL02

<400> SEQUENCE: 6

```
Thr Thr Tyr Lys Leu Val Ile Asn Gly Lys Thr Leu Lys Gly Glu Thr
1               5                   10                  15

Thr Thr Lys Ala Val Asp Ala Glu Thr Ala Glu Lys Ala Phe Lys Gln
            20                  25                  30

Tyr Ala Asn Asp Asn Gly Val Asp Gly Val Trp Thr Tyr Asp Asp Ala
        35                  40                  45

Thr Lys Thr Phe Thr Val Thr Glu Gly Gly Gly Ser Gly Gly Gly
    50                  55                  60

Gly Ser Gly Gly Gly Gly Ser Val Arg Glu Arg Gly Pro Gln Arg Val
65                  70                  75                  80

Ala Ala His Ile Thr Gly Thr Arg Gly Arg Ser Asn Thr Leu Ser Ser
                85                  90                  95

Pro Asn Ser Lys Asn Glu Lys Ala Leu Gly Arg Lys Ile Asn Ser Trp
                100                 105                 110

Glu Ser Ser Arg Ser Gly His Ser Phe Leu Ser Asn Leu His Leu Arg
            115                 120                 125

Asn Gly Glu Leu Val Ile Gln Glu Lys Gly Phe Tyr Tyr Ile Tyr Ser
130                 135                 140

Gln Thr Tyr Phe Arg Phe Gln Glu Glu Ile Lys Glu Asn Thr Lys Asn
145                 150                 155                 160

Asp Lys Gln Met Val Gln Tyr Ile Tyr Lys Tyr Thr Ser Tyr Pro Asp
                165                 170                 175

Pro Ile Leu Leu Met Lys Ser Ala Arg Asn Ser Cys Trp Ser Lys Asp
            180                 185                 190

Ala Glu Tyr Gly Leu Tyr Ser Ile Tyr Gln Gly Gly Leu Phe Glu Leu
        195                 200                 205

Lys Lys Asp Asp Arg Ile Phe Val Ser Val Thr Asn Glu His Leu Ile
    210                 215                 220

Asp Met Asp His Glu Ala Ser Phe Phe Gly Ala Phe Leu Val Gly
225                 230                 235
```

<210> SEQ ID NO 7
<211> LENGTH: 717
<212> TYPE: DNA
<213> ORGANISM: Homo sapiens
<220> FEATURE:
<221> NAME/KEY: misc_feature
<223> OTHER INFORMATION: IgBD-TRAIL01

<400> SEQUENCE: 7

```
accacctaca agctggtgat caacggcaag accctgaaag gcgagaccac caccaaagcg    60
gttgacgcgg agaccgcggc ggcggcgttc gcgcagtacg cgcgtcgcaa cggtgtggat   120
ggcgtttgga cctatgacga tgcgaccaag accttaccg tgaccgaagg cggaggcggt   180
tcaggcggag gtggctctgg cggtggcgga tcagtgagag aaagaggtcc tcagagagta   240
```

```
gcagctcaca taactgggac cagaggaaga agcaacacat tgtcttctcc aaactccaag    300
aatgaaaagg ctctgggccg caaaataaac tcctgggaat catcaaggag tgggcattca    360
ttcctgagca acttgcactt gaggaatggc gaactggtca tccaagaaaa ggggttttac    420
tacatctatt cccaaacata ctttcgattt caggaggaaa taaagaaaaa cacaaagaac    480
gacaaacaaa tggtccaata tatttacaaa tacacaagtt atcctgaccc tatactgctg    540
atgaaaagcg ctagaaatag ttgttggtct aaagatgcag aatacggact ctattccatc    600
tatcaagggg gattatttga gcttaagaaa gatgacagaa ttttgtttc tgtaacaaat     660 gagcacttga tagacatgga ccatgaagcc agcttttcg gggcctttt ggttggc        717
```

```
<210> SEQ ID NO 8
<211> LENGTH: 717
<212> TYPE: DNA
<213> ORGANISM: Homo sapiens
<220> FEATURE:
<221> NAME/KEY: misc_feature
<223> OTHER INFORMATION: IgBD-TRAIL02

<400> SEQUENCE: 8
accacctaca agctggtgat caacggcaag accctgaaag gcgagaccac caccaaagcg    60
gttgacgcgg agaccgcgga aaaggcgttc aaacagtacg cgaacgacaa cggtgtggat    120
ggcgtttgga cctatgacga tgcgaccaag acctttaccg tgaccgaagg cggaggcggt    180
tcaggcggag gtggctctgg cggtggcgga tcagtgagag aaagaggtcc tcagagagta    240
gcagctcaca taactgggac cagaggaaga agcaacacat tgtcttctcc aaactccaag    300
aatgaaaagg ctctgggccg caaaataaac tcctgggaat catcaaggag tgggcattca    360
ttcctgagca acttgcactt gaggaatggc gaactggtca tccaagaaaa ggggttttac    420
tacatctatt cccaaacata ctttcgattt caggaggaaa taaagaaaaa cacaaagaac    480
gacaaacaaa tggtccaata tatttacaaa tacacaagtt atcctgaccc tatactgctg    540
atgaaaagcg ctagaaatag ttgttggtct aaagatgcag aatacggact ctattccatc    600
tatcaagggg gattatttga gcttaagaaa gatgacagaa ttttgtttc tgtaacaaat     660 gagcacttga tagacatgga ccatgaagcc agcttttcg gggcctttt ggttggc        717
```

```
<210> SEQ ID NO 9
<211> LENGTH: 504
<212> TYPE: DNA
<213> ORGANISM: Homo sapiens
<220> FEATURE:
<221> NAME/KEY: misc_feature
<223> OTHER INFORMATION: TRAIL01

<400> SEQUENCE: 9
gtgagagaaa gaggtcctca gagagtagca gctcacataa ctgggaccag aggaagaagc    60
aacacattgt cttctccaaa ctccaagaat gaaaaggctc tgggccgcaa aataaactcc    120
tgggaatcat caaggagtgg gcattcattc ctgagcaact tgcacttgag gaatggcgaa    180
ctggtcatcc aagaaaaggg ttttactac atctattccc aaacatactt tcgatttcag    240
gaggaaataa agaaaacac aaagaacgac aaacaaatgg tccaatatat ttacaaatac    300
acaagttatc ctgaccctat actgctgatg aaaagcgcta gaaatagttg ttggtctaaa    360
gatgcagaat acggactcta ttccatctat caaggggat tatttgagct taagaaagat    420
gacagaattt tgtttctgt aacaaatgag cacttgatag acatggacca tgaagccagc    480
ttttcggggg ccttttggt tggc                                           504
```

<210> SEQ ID NO 10
<211> LENGTH: 168
<212> TYPE: DNA
<213> ORGANISM: Homo sapiens
<220> FEATURE:
<221> NAME/KEY: misc_feature
<223> OTHER INFORMATION: IgBD 01

<400> SEQUENCE: 10

| | | | | | |
|---|---|---|---|---|---|
| accacctaca | agctggtgat | caacggcaag | accctgaaag | gcgagaccac | caccaaagcg | 60 |
| gttgacgcgg | agaccgcggc | ggcggcgttc | gcgcagtacg | cgcgtcgcaa | cggtgtggat | 120 |
| ggcgtttgga | cctatgacga | tgcgaccaag | acctttaccg | tgaccgaa | | 168 |

<210> SEQ ID NO 11
<211> LENGTH: 168
<212> TYPE: DNA
<213> ORGANISM: Homo sapiens
<220> FEATURE:
<221> NAME/KEY: misc_feature
<223> OTHER INFORMATION: IgBD 02

<400> SEQUENCE: 11

| | | | | | |
|---|---|---|---|---|---|
| accacctaca | agctggtgat | caacggcaag | accctgaaag | gcgagaccac | caccaaagcg | 60 |
| gttgacgcgg | agaccgcgga | aaaggcgttc | aaacagtacg | cgaacgacaa | cggtgtggat | 120 |
| ggcgtttgga | cctatgacga | tgcgaccaag | acctttaccg | tgaccgaa | | 168 |

<210> SEQ ID NO 12
<211> LENGTH: 45
<212> TYPE: DNA
<213> ORGANISM: Homo sapiens
<220> FEATURE:
<221> NAME/KEY: misc_feature
<223> OTHER INFORMATION: (G4S)3

<400> SEQUENCE: 12
ggcggaggcg gttcaggcgg aggtggctct ggcggtggcg gatca                45

<210> SEQ ID NO 13
<211> LENGTH: 504
<212> TYPE: DNA
<213> ORGANISM: Homo sapiens
<220> FEATURE:
<221> NAME/KEY: misc_feature
<223> OTHER INFORMATION: TRAIL02

<400> SEQUENCE: 13

| | | | | | |
|---|---|---|---|---|---|
| gtgagagaaa | gaggtcctca | gagagtagca | gctcacataa | ctgggaccag | aggaagaagc | 60 |
| aacacattgt | cttctccaaa | ctccaagaat | gaaaaggctc | tgggccgcaa | aataaactcc | 120 |
| tgggaatcat | caaggagtgg | gcattcattc | ctgagcaact | tgcacttgag | gaatggtgaa | 180 |
| ctggtcatcc | atgaaaaagg | ttttactac | atctattccc | aaacatactt | tcgatttcag | 240 |
| gaggaaataa | agaaaacac | aaagaacgac | aaacaaatgg | tccaatatat | ttacaaatac | 300 |
| acaagttatc | ctgaccctat | attgttgatg | aaaagtgcta | gaaatagttg | ttggtctaaa | 360 |
| gatgcagaat | atggactcta | ttccatctat | caaggggaa | tatttgagct | taaggaaaat | 420 |
| gacagaattt | ttgtttctgt | aacaaatgag | cacttgatag | acatggacca | tgaagccagt | 480 |
| tttttcgggg | cctttttagt | tggc | | | | 504 |

<210> SEQ ID NO 14

<211> LENGTH: 168
<212> TYPE: PRT
<213> ORGANISM: Homo sapiens
<220> FEATURE:
<221> NAME/KEY: misc_feature
<223> OTHER INFORMATION: TRAIL02

<400> SEQUENCE: 14

Val Arg Glu Arg Gly Pro Gln Arg Val Ala Ala His Ile Thr Gly Thr
1               5                   10                  15

Arg Gly Arg Ser Asn Thr Leu Ser Ser Pro Asn Ser Lys Asn Glu Lys
            20                  25                  30

Ala Leu Gly Arg Lys Ile Asn Ser Trp Glu Ser Ser Arg Ser Gly His
        35                  40                  45

Ser Phe Leu Ser Asn Leu His Leu Arg Asn Gly Glu Leu Val Ile His
    50                  55                  60

Glu Lys Gly Phe Tyr Tyr Ile Tyr Ser Gln Thr Tyr Phe Arg Phe Gln
65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
    130                 135                 140

Val Ser Val Thr Asn Glu His Leu Ile Asp Met Asp His Glu Ala Ser
145                 150                 155                 160

Phe Phe Gly Ala Phe Leu Val Gly
                165

<210> SEQ ID NO 15
<211> LENGTH: 717
<212> TYPE: DNA
<213> ORGANISM: Homo sapiens
<220> FEATURE:
<221> NAME/KEY: misc_feature
<223> OTHER INFORMATION: IgBD-TRAIL03

<400> SEQUENCE: 15
accacctaca agctggtgat caacggcaag accctgaaag gcgagaccac caccaaagcg      60
gttgacgcgg agaccgcggc ggcggcgttc gcgcagtacg cgcgtcgcaa cggtgtggat     120
ggcgtttgga cctatgacga tgcgaccaag acctttaccg tgaccgaagg cggaggcggt     180
tcaggcggag gtggctctgg cggtggcgga tcagtgagag aaagaggtcc tcagagagta     240
gcagctcaca taactgggac cagaggaaga agcaacacat gtcttctcc aaactccaag      300 aatgaaaagg ctctgggccg caaaataaac tcctgggaat catcaaggag tgggcattca     360
ttcctgagca acttgcactt gaggaatggt gaactggtca tccatgaaaa agggttttac     420
tacatctatt cccaaacata ctttcgattt caggaggaaa taaagaaaa cacaaagaac      480 gacaaacaaa tggtccaata tatttacaaa tacacaagtt atcctgaccc tatattgttg     540
atgaaaagtg ctagaaatag ttgttggtct aaagatgcag aatatggact ctattccatc     600
tatcaagggg gaatatttga gcttaaggaa aatgacagaa ttttgttc tgtaacaaat       660 gagcacttga tagacatgga ccatgaagcc agtttttcg ggccttttt agttggc         717

<210> SEQ ID NO 16

```
<211> LENGTH: 239
<212> TYPE: PRT
<213> ORGANISM: Homo sapiens
<220> FEATURE:
<221> NAME/KEY: misc_feature
<223> OTHER INFORMATION: IgBD-TRAIL03

<400> SEQUENCE: 16

Thr Thr Tyr Lys Leu Val Ile Asn Gly Lys Thr Leu Lys Gly Glu Thr
1               5                   10                  15

Thr Thr Lys Ala Val Asp Ala Glu Thr Ala Ala Ala Phe Ala Gln
            20                  25                  30

Tyr Ala Arg Arg Asn Gly Val Asp Gly Val Trp Thr Tyr Asp Asp Ala
            35                  40                  45

Thr Lys Thr Phe Thr Val Thr Glu Gly Gly Gly Ser Gly Gly Gly
        50                  55                  60

Gly Ser Gly Gly Gly Ser Val Arg Glu Arg Gly Pro Gln Arg Val
65              70                  75                  80

Ala Ala His Ile Thr Gly Thr Arg Gly Arg Ser Asn Thr Leu Ser Ser
                85                  90                  95

Pro Asn Ser Lys Asn Glu Lys Ala Leu Gly Arg Lys Ile Asn Ser Trp
                100                 105                 110

Glu Ser Ser Arg Ser Gly His Ser Phe Leu Ser Asn Leu His Leu Arg
            115                 120                 125

Asn Gly Glu Leu Val Ile His Glu Lys Gly Phe Tyr Tyr Ile Tyr Ser
        130                 135                 140

Gln Thr Tyr Phe Arg Phe Gln Glu Glu Ile Lys Glu Asn Thr Lys Asn
145                 150                 155                 160

Asp Lys Gln Met Val Gln Tyr Ile Tyr Lys Tyr Thr Ser Tyr Pro Asp
                165                 170                 175

Pro Ile Leu Leu Met Lys Ser Ala Arg Asn Ser Cys Trp Ser Lys Asp
                180                 185                 190

Ala Glu Tyr Gly Leu Tyr Ser Ile Tyr Gln Gly Gly Ile Phe Glu Leu
            195                 200                 205

Lys Glu Asn Asp Arg Ile Phe Val Ser Val Thr Asn Glu His Leu Ile
210                 215                 220

Asp Met Asp His Glu Ala Ser Phe Phe Gly Ala Phe Leu Val Gly
225                 230                 235

<210> SEQ ID NO 17
<211> LENGTH: 138
<212> TYPE: DNA
<213> ORGANISM: Homo sapiens
<220> FEATURE:
<221> NAME/KEY: misc_feature
<223> OTHER INFORMATION: ABD

<400> SEQUENCE: 17
ctggctgaag caaaagtcct ggcgaatcgt gaactggata agtatggcgt ctcggatttc      60
tacaagcgtc tgatcaataa agcaaaaacc gtggaaggcg ttgaagcact gaaactgcat     120
attctggccg cactgccg                                                    138

<210> SEQ ID NO 18
<211> LENGTH: 46
<212> TYPE: PRT
<213> ORGANISM: Homo sapiens
<220> FEATURE:
<221> NAME/KEY: misc_feature
<223> OTHER INFORMATION: ABD
```

-continued

<400> SEQUENCE: 18

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 19
<211> LENGTH: 687
<212> TYPE: DNA
<213> ORGANISM: Homo sapiens
<220> FEATURE:
<221> NAME/KEY: misc_feature
<223> OTHER INFORMATION: ABD-TRAIL01

<400> SEQUENCE: 19
ctggctgaag caaaagtcct ggcgaatcgt gaactggata gtatggcgt ctcggatttc      60 tacaagcgtc tgatcaataa agcaaaaacc gtggaaggcg ttgaagcact gaaactgcat    120
attctggccg cactgccggg cggaggcggt tcaggcggag gtggctctgg cgtggcgga    180 tcagtgagag aaagaggtcc tcagagagta gcagctcaca taactgggac cagaggaaga    240
agcaacacat tgtcttctcc aaactccaag aatgaaaagg ctctgggccg caaaataaac    300
tcctgggaat catcaaggag tgggcattca ttcctgagca acttgcactt gaggaatggc    360
gaactggtca tccaagaaaa ggggttttac tacatctatt cccaaacata ctttcgattt    420
caggaggaaa taaagaaaaa cacaaagaac gacaaacaaa tggtccaata tatttacaaa    480
tacacaagtt atcctgaccc tatactgctg atgaaaagcg ctagaaatag ttgttggtct    540
aaagatgcag aatacggact ctattccatc tatcaagggg gattatttga gcttaagaaa    600
gatgacagaa ttttttgttt tgtaacaaat gagcacttga tagacatgga ccatgaagcc    660 agcttttttcg gggccttttt ggttggc                                       687

<210> SEQ ID NO 20
<211> LENGTH: 229
<212> TYPE: PRT
<213> ORGANISM: Homo sapiens
<220> FEATURE:
<221> NAME/KEY: misc_feature
<223> OTHER INFORMATION: ABD-TRAIL01

<400> SEQUENCE: 20

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro Gly Gly
        35                  40                  45

Gly Gly Ser Gly Gly Gly Gly Ser Gly Gly Gly Ser Val Arg Glu
    50                  55                  60

Arg Gly Pro Gln Arg Val Ala Ala His Ile Thr Gly Thr Arg Gly Arg
65                  70                  75                  80

Ser Asn Thr Leu Ser Ser Pro Asn Ser Lys Asn Glu Lys Ala Leu Gly
                85                  90                  95

Arg Lys Ile Asn Ser Trp Glu Ser Ser Arg Ser Gly His Ser Phe Leu
            100                 105                 110

```
Ser Asn Leu His Leu Arg Asn Gly Glu Leu Val Ile Gln Glu Lys Gly
            115                 120                 125

Phe Tyr Tyr Ile Tyr Ser Gln Thr Tyr Phe Arg Phe Gln Glu Glu Ile
        130                 135                 140

Lys Glu Asn Thr Lys Asn Asp Lys Gln Met Val Gln Tyr Ile Tyr Lys
145                 150                 155                 160

Tyr Thr Ser Tyr Pro Asp Pro Ile Leu Leu Met Lys Ser Ala Arg Asn
                165                 170                 175

Ser Cys Trp Ser Lys Asp Ala Glu Tyr Gly Leu Tyr Ser Ile Tyr Gln
            180                 185                 190

Gly Gly Leu Phe Glu Leu Lys Lys Asp Asp Arg Ile Phe Val Ser Val
        195                 200                 205

Thr Asn Glu His Leu Ile Asp Met Asp His Glu Ala Ser Phe Phe Gly
210                 215                 220

Ala Phe Leu Val Gly
225

<210> SEQ ID NO 21
<211> LENGTH: 399
<212> TYPE: DNA
<213> ORGANISM: Homo sapiens
<220> FEATURE:
<221> NAME/KEY: misc_feature
<223> OTHER INFORMATION: IL2

<400> SEQUENCE: 21
gcacctactt caagttctac aaagaaaaca cagctacaac tggagcattt actgctggat      60
ttacagatga ttttgaatgg aattaataat tacaagaatc ccaaactcac caggatgctc     120
acatttaagt tttacatgcc caagaaggcc acagaactga acatcttca gtgtctagaa      180 gaagaactca aacctctgga ggaagtgcta aatttagctc aaagcaaaaa ctttcactta     240
agacccaggg acttaatcag caatatcaac gtaatagttc tggaactaaa gggatctgaa     300
acaacattca tgtgtgaata tgctgatgag acagcaacca ttgtagaatt tctgaacaga     360
tggattacct tttgtcaaag catcatctca acactgact                            399

<210> SEQ ID NO 22
<211> LENGTH: 133
<212> TYPE: PRT
<213> ORGANISM: Homo sapiens
<220> FEATURE:
<221> NAME/KEY: misc_feature
<223> OTHER INFORMATION: IL2

<400> SEQUENCE: 22

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
```

```
            100                 105                 110
Thr Ile Val Glu Phe Leu Asn Arg Trp Ile Thr Phe Cys Gln Ser Ile
            115                 120                 125

Ile Ser Thr Leu Thr
            130
```

<210> SEQ ID NO 23
<211> LENGTH: 612
<212> TYPE: DNA
<213> ORGANISM: Homo sapiens
<220> FEATURE:
<221> NAME/KEY: misc_feature
<223> OTHER INFORMATION: IgBD-IL2

<400> SEQUENCE: 23

```
accacctaca agctggtgat caacggcaag accctgaaag gcgagaccac caccaaagcg     60
gttgacgcgg agaccgcggc ggcggcgttc gcgcagtacg cgcgtcgcaa cggtgtggat    120
ggcgtttgga cctatgacga tgcgaccaag acctttaccg tgaccgaagg cggaggcggt    180
tcaggcggag gtggctctgg cggtggcgga tcagcaccta cttcaagttc tacaaagaaa    240
acacagctac aactggagca tttactgctg gattttagag tgattttgaa tggaattaat    300
aattacaaga atcccaaact caccaggatg ctcacattta agttttacat gcccaagaag    360
gccacagaac tgaaacatct tcagtgtcta gaagaagaac tcaaacctct ggaggaagtg    420
ctaaatttag ctcaaagcaa aaactttcac ttaagaccca gggacttaat cagcaatatc    480
aacgtaatag ttctggaact aaagggatct gaaacaacat tcatgtgtga atatgctgat    540
gagacagcaa ccattgtaga atttctgaac agatggatta ccttttgtca agcatcatc    600
tcaacactga ct                                                        612
```

<210> SEQ ID NO 24
<211> LENGTH: 204
<212> TYPE: PRT
<213> ORGANISM: Homo sapiens
<220> FEATURE:
<221> NAME/KEY: misc_feature
<223> OTHER INFORMATION: IgBD-IL2

<400> SEQUENCE: 24

```
Thr Thr Tyr Lys Leu Val Ile Asn Gly Lys Thr Leu Lys Gly Glu Thr
1               5                   10                  15

Thr Thr Lys Ala Val Asp Ala Glu Thr Ala Ala Ala Phe Ala Gln
            20                  25                  30

Tyr Ala Arg Arg Asn Gly Val Asp Gly Val Trp Thr Tyr Asp Asp Ala
            35                  40                  45

Thr Lys Thr Phe Thr Val Thr Glu Gly Gly Gly Ser Gly Gly Gly
        50                  55                  60

Gly Ser Gly Gly Gly Gly Ser Ala Pro Thr Ser Ser Ser Thr Lys Lys
65                  70                  75                  80

Thr Gln Leu Gln Leu Glu His Leu Leu Leu Asp Leu Gln Met Ile Leu
            85                  90                  95

Asn Gly Ile Asn Asn Tyr Lys Asn Pro Lys Leu Thr Arg Met Leu Thr
            100                 105                 110

Phe Lys Phe Tyr Met Pro Lys Lys Ala Thr Glu Leu Lys His Leu Gln
            115                 120                 125

Cys Leu Glu Glu Glu Leu Lys Pro Leu Glu Glu Val Leu Asn Leu Ala
            130                 135                 140
```

```
Gln Ser Lys Asn Phe His Leu Arg Pro Arg Asp Leu Ile Ser Asn Ile
145                 150                 155                 160

Asn Val Ile Val Leu Glu Leu Lys Gly Ser Glu Thr Thr Phe Met Cys
            165                 170                 175

Glu Tyr Ala Asp Glu Thr Ala Thr Ile Val Glu Phe Leu Asn Arg Trp
            180                 185                 190

Ile Thr Phe Cys Gln Ser Ile Ile Ser Thr Leu Thr
            195                 200

<210> SEQ ID NO 25
<211> LENGTH: 39
<212> TYPE: DNA
<213> ORGANISM: Homo sapiens
<220> FEATURE:
<221> NAME/KEY: misc_feature
<223> OTHER INFORMATION: Fc3

<400> SEQUENCE: 25
gactgtgcgt ggcacctggg agaattggtg tggtgtaca                        39

<210> SEQ ID NO 26
<211> LENGTH: 13
<212> TYPE: PRT
<213> ORGANISM: Homo sapiens
<220> FEATURE:
<221> NAME/KEY: misc_feature
<223> OTHER INFORMATION: Fc3

<400> SEQUENCE: 26

Asp Cys Ala Trp His Leu Gly Glu Leu Val Trp Cys Thr
1               5                   10

<210> SEQ ID NO 27
<211> LENGTH: 588
<212> TYPE: DNA
<213> ORGANISM: Homo sapiens
<220> FEATURE:
<221> NAME/KEY: misc_feature
<223> OTHER INFORMATION: Fc3-TRAIL01

<400> SEQUENCE: 27
gactgtgcgt ggcacctggg agaattggtg tggtgtacag gcggaggcgg ttcaggcgga      60
ggtggctctg gcggtggcgg atcagtgaga gaaagaggtc ctcagagagt agcagctcac     120
ataactggga ccagaggaag aagcaacaca ttgtcttctc caaactccaa gaatgaaaag     180
gctctgggcc gcaaaataaa ctcctgggaa tcatcaagga gtgggcattc attcctgagc     240
aacttgcact tgaggaatgg cgaactggtc atccaagaaa aggggtttta ctacatctat     300
tcccaaacat actttcgatt tcaggaggaa ataaaagaaa acacaaagaa cgacaaacaa     360
atggtccaat atatttacaa atacacaagt tatcctgacc ctatactgct gatgaaaagc     420
gctagaaata gttgttggtc taaagatgca gaatacggac tctattccat ctatcaaggg     480
ggattatttg agcttaagaa agatgacaga atttttgttt ctgtaacaaa tgagcacttg     540
atagacatgg accatgaagc cagctttttc ggggccttt tggttggc                  588

<210> SEQ ID NO 28
<211> LENGTH: 196
<212> TYPE: PRT
<213> ORGANISM: Homo sapiens
<220> FEATURE:
<221> NAME/KEY: misc_feature
<223> OTHER INFORMATION: Fc3-TRAIL01
```

```
<400> SEQUENCE: 28

Asp Cys Ala Trp His Leu Gly Glu Leu Val Trp Cys Thr Gly Gly Gly
1               5                   10                  15

Gly Ser Gly Gly Gly Ser Gly Gly Gly Ser Val Arg Glu Arg
            20                  25                  30

Gly Pro Gln Arg Val Ala Ala His Ile Thr Gly Thr Arg Gly Arg Ser
        35                  40                  45

Asn Thr Leu Ser Ser Pro Asn Ser Lys Asn Glu Lys Ala Leu Gly Arg
    50                  55                  60

Lys Ile Asn Ser Trp Glu Ser Ser Arg Ser Gly His Ser Phe Leu Ser
65                  70                  75                  80

Asn Leu His Leu Arg Asn Gly Glu Leu Val Ile Gln Glu Lys Gly Phe
                85                  90                  95

Tyr Tyr Ile Tyr Ser Gln Thr Tyr Phe Arg Phe Gln Glu Glu Ile Lys
            100                 105                 110

Glu Asn Thr Lys Asn Asp Lys Gln Met Val Gln Tyr Ile Tyr Lys Tyr
            115                 120                 125

Thr Ser Tyr Pro Asp Pro Ile Leu Leu Met Lys Ser Ala Arg Asn Ser
        130                 135                 140

Cys Trp Ser Lys Asp Ala Glu Tyr Gly Leu Tyr Ser Ile Tyr Gln Gly
145                 150                 155                 160

Gly Leu Phe Glu Leu Lys Lys Asp Asp Arg Ile Phe Val Ser Val Thr
                165                 170                 175

Asn Glu His Leu Ile Asp Met Asp His Glu Ala Ser Phe Phe Gly Ala
            180                 185                 190

Phe Leu Val Gly
        195
```

FUSION PROTEIN CONTAINING TRAIL AND IgG BINDING DOMAIN AND THE USES THEREOF

INCORPORATION OF SEQUENCE LISTING

This application contains a sequence listing submitted in Computer Readable Form (CRF). The CFR file contains the sequence listing entitled "PA288-0051_ST25.txt", which was created on Aug. 10, 2020, and is 28,917 bytes in size. The information in the sequence listing is incorporated herein by reference in its entirety.

TECHNICAL FIELD

The present invention belongs to the field of biodrugs, in particular to a fusion protein containing TRAIL and IgG-binding domain, as well as the use thereof.

BACKGROUND ART

TRAIL is a member of tumor necrosis factor (TNF) superfamily. TRAIL has four membrane receptors, namely TRAIL R1, R2, R3 and R4. Among these receptors, only TRAIL R1 (DR4) and R2 (DR5) are death receptors (DR), which contain complete death domain. Once engaged with TRAIL, the death receptor is activated followed by triggering the death pathways in the cells through the death domain to induce apoptosis. However, TRAIL R3 (DcR1) and R4 (DcR2) are decoy receptors (DcR) with incomplete death domain or lacking death domain. These decoy receptors can't trigger death signal after binding with TRAIL (Wiezorek et al. Clin Cancer Res. 2010; 16: 1701-8; Oikonomou et al., BioFactors. 2013; 39: 343-54). Death receptors DR4 and/or DR5 are generally and highly expressed in tumor cells, while decoy receptors DcR1 and DcR2 are highly expressed in normal cells. Moreover, the binding ability of TRAIL to death receptor is much higher than that of decoy receptor. Therefore, TRAIL induced apoptosis of tumor cells at low concentration. However, TRAIL showed little toxicities in normal cells. TRAIL is an ideal candidate for antitumor drugs (Wajant et al., Cancer Lett. 2013; 332: 163-74; Lim et al. Expert Opin Ther Targets. 2015; 19: 1171-85).

TRAIL can be divided into two types, i.e. membrane-bound type and soluble type. Membrane-bound type of TRAIL consists of 281 amino acids, including an N-terminal hydrophobic transmembrane domain and a C-terminal hydrophilic extracellular domain. Membrane-bound TRAIL is predominantly expressed on the surface of immune cells (such as T cells and natural killer cells). The extracellular domain of membrane-bound TRAIL might be cleaved from the cell membrane to produce soluble TRAIL in the blood. In vitro experiments showed that the recombinant soluble TRAIL could induce apoptosis of a variety of tumor cells at low concentration of nM. However, TRAIL had no obvious cytotoxicity in normal cells even at the high concentration of μM. Clinical trials have also shown that TRAIL showed good safety. However, the antitumor effect of TRAIL in vivo, especially in patients, is far from the expectation, which is mismatch with its super in vitro cytotoxicity in tumor cells. "Short half-life" is considered to be the primary reason for the unsatisfactory anti-tumor effect of TRAIL in vivo. It was proved that the half-life of TRAIL is approximately of ten minutes in experimental animals, and less than one hour in human body (Stuckey et al., Trends Mol Med. 2013; 19: 685-94; Lim et al. Expert Opin Ther Targets. 2015; 19: 1171-85). Therefore, prolonging the half-life of TRAIL is likely to improve the antitumor effect of TRAIL in vivo, which would promote the clinical application of TRAIL.

In order to prolong its half-life, researchers have modified TRAIL by various methods. These methods include: modification with polyethylene glycol (PEG), glycan, or nano material, fusion/conjugating/binding to Fc and albumin, etc. For example, Kim et al. (Biocon Chem. 2011; 22: 1631-7) extended the half-life of TRAIL by 10-20 times using in situ PEGylation with PEG of 20 kDa or more. Wang et al. (Mol Cancer Ther, 2014; 13: 643-50) extended the half-life of TRAIL by about 10 times through Fc fusion. Muller et al. (Biochem Biophys Res Communn, 2010; 396: 793-9) fused TRAIL with albumin, which also prolonged its half-life by about 15 times. All these methods prolonged the half-life of TRAIL and improved its antitumor effect in vivo. However, the problems of PEGylation, Fc or albumin fusion, as well as conjugating to albumin include complexity of process, low yield of heterogeneous recombinant product, and high cost, etc.

It was found that IgG antibody in blood can bind to its receptor FcRn to form a complex that can escape from lysosomal degradation under acidic condition of endosome after entering the cells. Subsequently, IgG-FcRn complex can be delivered outside the cell. At that time, IgG is released and enters the blood circulation again. This process is called FcRn-mediated recycling. Generally, the half-lives of most natural proteins are only a few minutes or hours. However, FcRn-mediated recycling results in a super long half-life (2-3 weeks) of IgG (Pyzik et al. J Immunol, 2015; 194: 4595-603; Sockolosky et al., Adv Drug Deliv Rev. 2015; 91: 109-24). In addition, IgG antibody can also mediate antibody-dependent cell killing (Wang et al. Front Immunol. 2015; 6: 368). Therefore, if IgG antibody is used as a carrier, it is possible not only to prolong the half-life of the drug, improve drug targeting, but also introduce the antibody actions of killing the target cells.

In order to use antibodies as carriers of TRAIL, the traditional method is to fuse the antibody or antibody fragment to TRAIL. However, this strategy, especially fusing TRAIL to intact antibody is limited by the difficulty of techniques, low yield of recombinant product, long preparative cycle, and high cost due to the super high molecular weight of the recombinant product (Siegemund M et al, Mabs, 2016, 8: 879-891; Siegemund M et al, Scientific report, 2018, 8: 7808).

CONTENT OF THE INVENTION

To solve above problems, the present invention is aimed to fuse an IgG-binding domain (a small peptide with IgG-binding ability) to TRAIL to endow TRAIL with IgG-binding ability. The modified TRAIL with IgG-binding ability showed prolonged half-life, enhanced tumor-targeting, and improved in vivo antitumor effects, when it binds to endogenous IgG after injected into the body, or binds to exogenous IgG.

In particular: The present invention provides a recombinant IgBD-TRAIL protein and the use thereof.

IgG is the abbreviation of immunoglobulin G.

IgBD is IgG-binding domain.

TRAIL is TNF-related apoptosis-inducing ligand that can high efficiently and selectively kill tumor cells.

Protein G is streptococcal protein G, a cell wall protein on the surface of streptococci.

The present invention provides a fusion protein, that contains:

(1) TRAIL functional domain (a) or the domains with at least 80% homology with the TRAIL functional domain (a);

And (2) The IgG-binding domain (b) or the domain with at least 80% homology with IgG-binding domain (b);

Preferably, said TRAIL is derived from monkey or human; the IgG-binding domain (b) comes from *Streptococcus* protein G; and the domain (b) is fused to the N-terminal of domain (a) through a linker.

Wherein, it contains:

(1) The domains with at least 90% homology with TRAIL functional domain (a);

And (2) The domain with at least 90% homology with the IgG-binding domain (b).

Wherein, the amino acid sequence of the TRAIL functional domain (a) is shown in SEQ ID No: 1 or 14.

Wherein, the amino acid sequence of the IgG-binding domain is shown in SEQ ID No: 2 or 3.

Wherein, the linker is a $(G4S)_3$ linker, whose amino acid sequence is shown in SEQ ID No: 4.

Wherein, its amino acid sequence is shown as any one of SEQ ID NO:5, 6 or 16.

Wherein, it is encoded by the nucleotide sequence shown as any one of SEQ ID No: 7, 8 or 15.

The present invention also provides a nucleotide sequence, that contains:

(1) The gene coding sequence of the TRAIL functional domain (a) or the domain with at least 80% homology with TRAIL functional domain (a);

And (2) The gene coding sequence of the IgG-binding domain (b) or the domain with at least 80% homology with IgG-binding domain (b);

Preferably, the TRAIL functional domain is derived from monkey or human TRAIL; the IgG-binding domain (b) comes from *Streptococcus* protein G.

Wherein, it contains (1) the gene coding sequence of the domains with at least 90% homology with TRAIL functional domain (a);

And (2) the gene coding sequence of the domain with at least 90% homology with the IgG-binding domain (b).

Wherein, the gene coding sequence of TRAIL functional domain is shown in SEQ ID NO:9 or 13.

Wherein, the gene coding sequence of the IgG-binding domain (b) is shown in SEQ ID NO:10 or 11.

Wherein, the linker is a $(G4S)_3$ linker, whose gene coding sequence is shown in SEQ ID No: 12.

Wherein, its nucleotide sequence is shown as any one of SEQ ID NO:7, 8 or 15.

The present invention also provides a recombinant vector containing the nucleotide sequence mentioned above.

Wherein, said recombinant vector is a recombinant plasmid or a genetic engineering vector; preferably, the recombinant plasmid is a recombinant pQE30 plasmid.

The present invention further provides a recombinant expression host cell containing the recombinant vector mentioned above.

Wherein, said recombinant expression host cells include *Escherichia coli*.

The present invention provides the use of the fusion protein mentioned above in the preparation of a drug for treatment of tumor.

Wherein, the drug for treatment of tumors includes those treating colon cancer, rectal adenocarcinoma, breast cancer, lung cancer, and liver cancer.

The present invention further provides an anti-tumor drug, characterized in that it is a preparation prepared by using the fusion protein mentioned above as the active component, with the addition of pharmaceutically acceptable excipients.

The anti-tumor drug mentioned above also includes the antibodies of immunoglobulin G.

Further, said IgG antibodies include antibodies against EGFR or CD47.

Finally, the present invention provides an anti-tumor drug combination, that contains the same or different specifications of preparations for simultaneous or separate administration of above-mentioned drugs and other classes of anti-tumor drugs, as well as pharmaceutically acceptable carriers; preferably, said other classes of anti-tumor drugs are IgG antibodies.

Wherein, said IgG antibodies include antibodies against EGFR or CD47.

The recombinant protein of the present invention has strong anti-tumor activity, high stability and long half-life in vivo, and can exert better anti-tumor effect than TRAIL.

The present invention can also be used in combination with other types of anti-tumor drugs to produce a synergistic effect, which have good antitumor effects and an excellent market prospect.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

Figure 11:
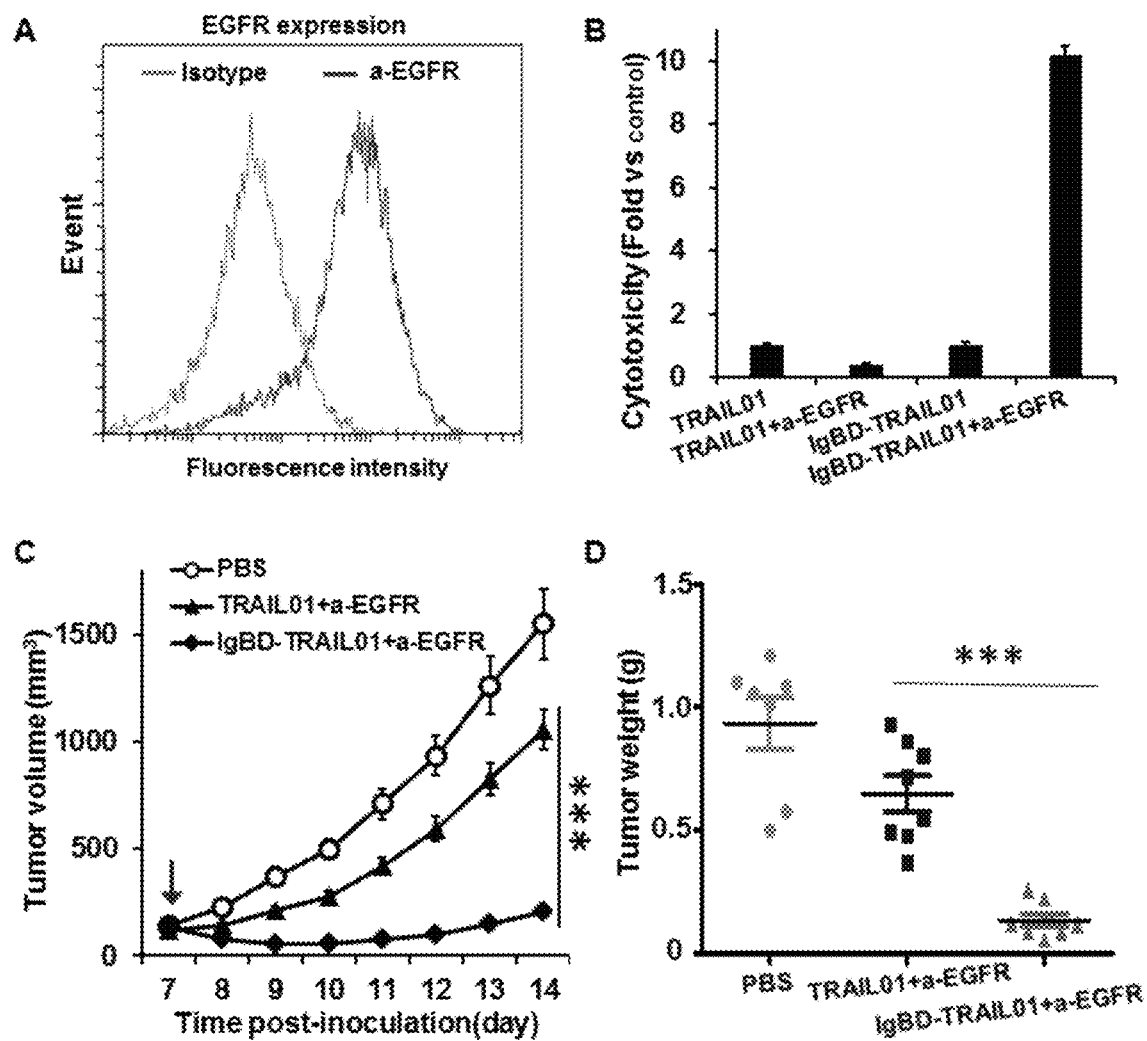
Figure 12:
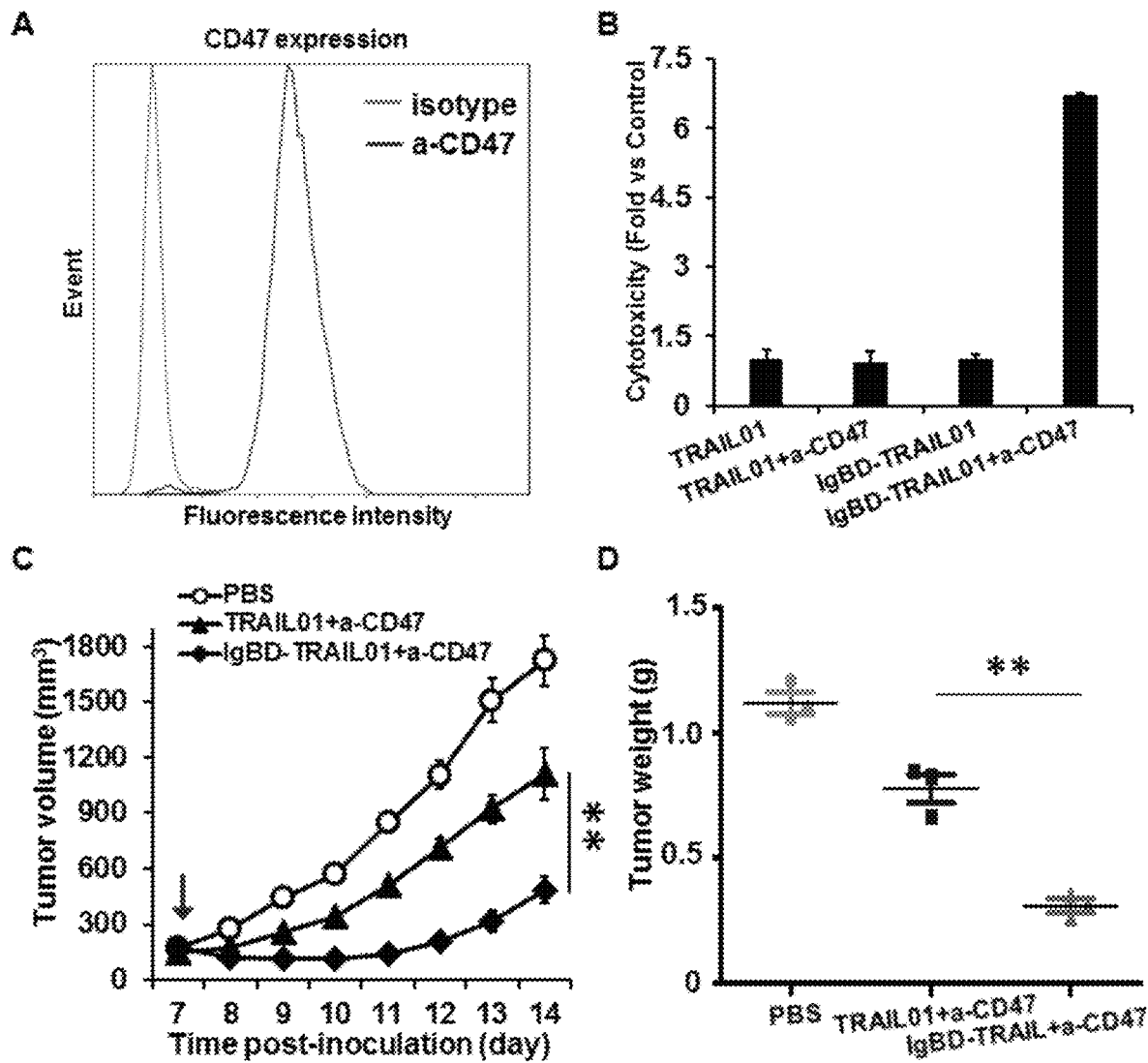
Figure 13:
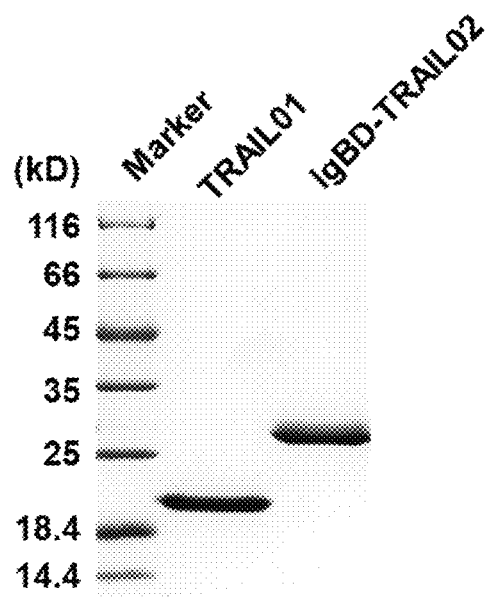
Figure 14:
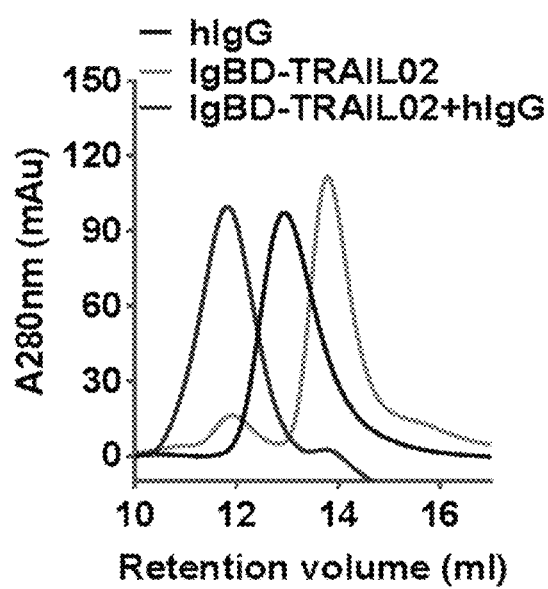
Figure 15:
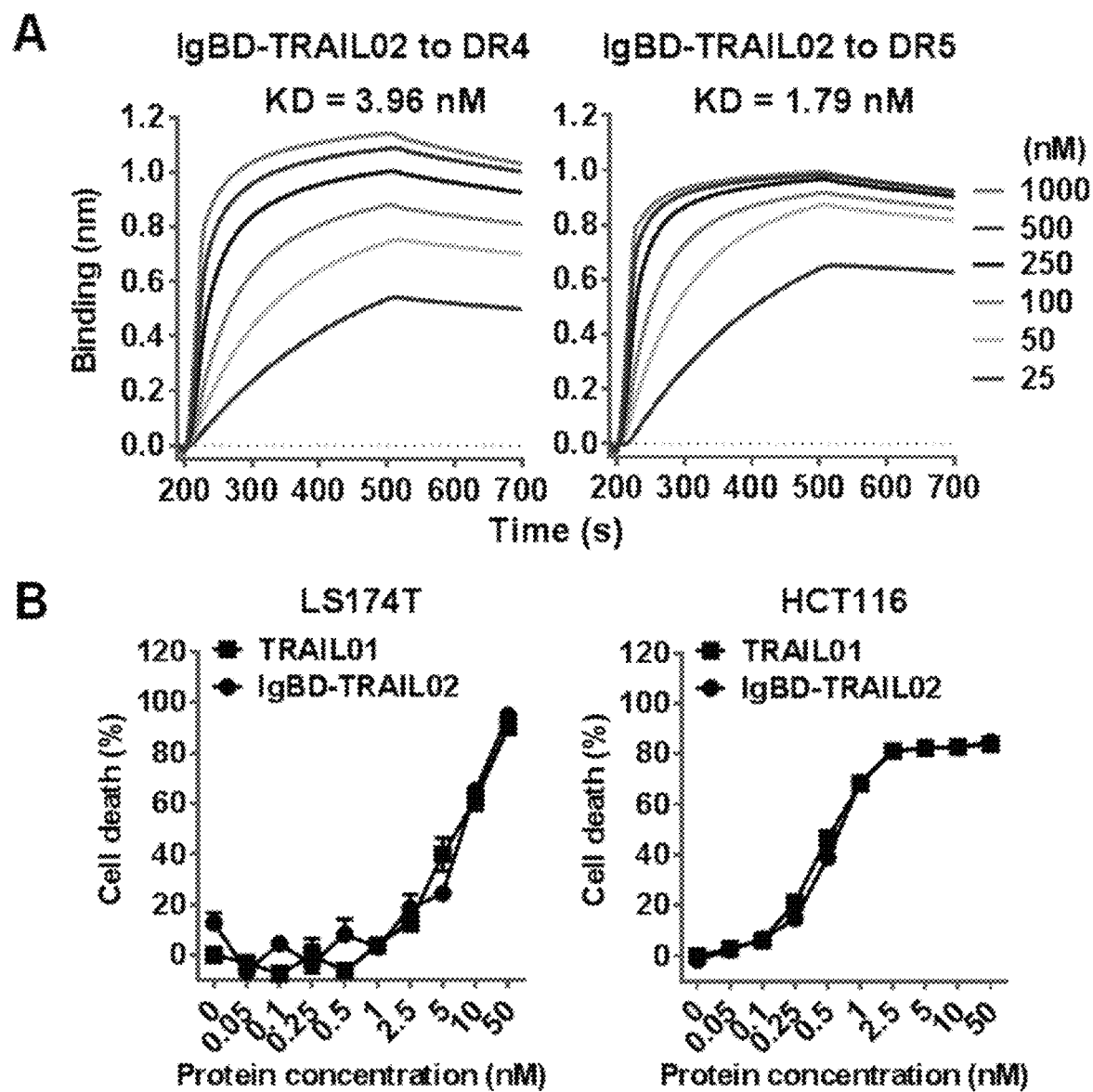
Figure 16:
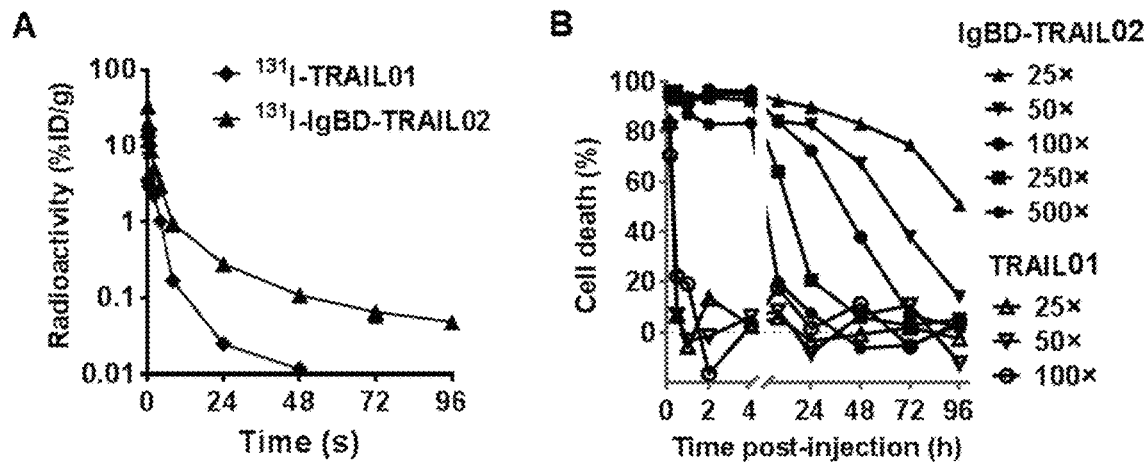
Figure 17:
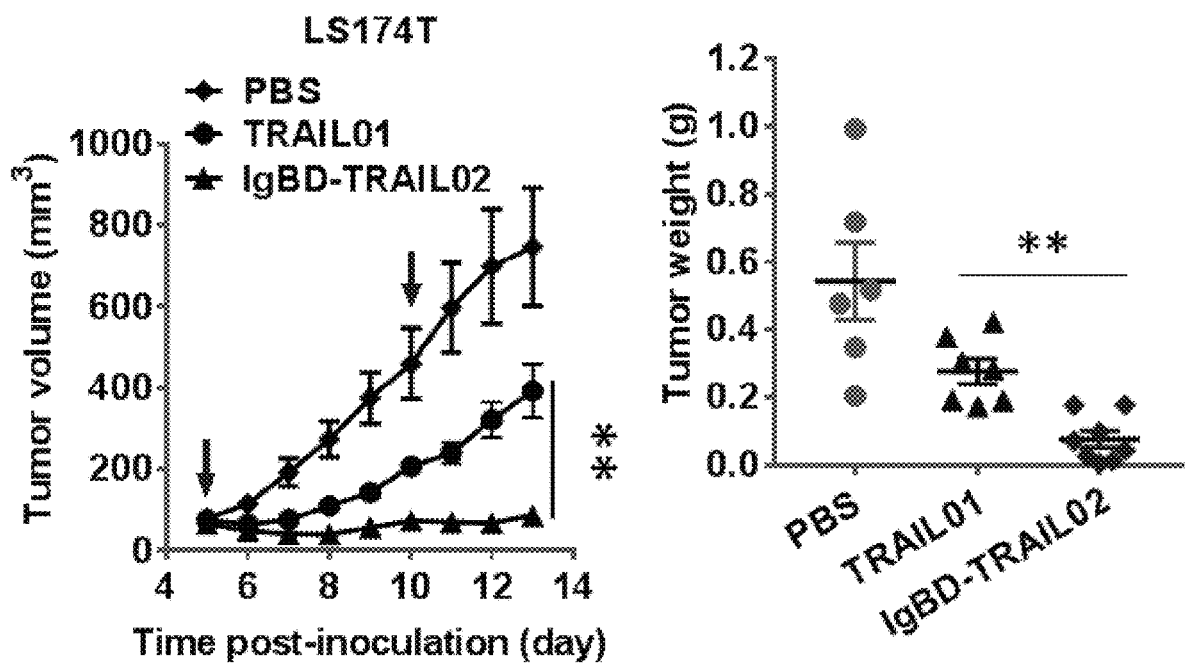
Figure 18:
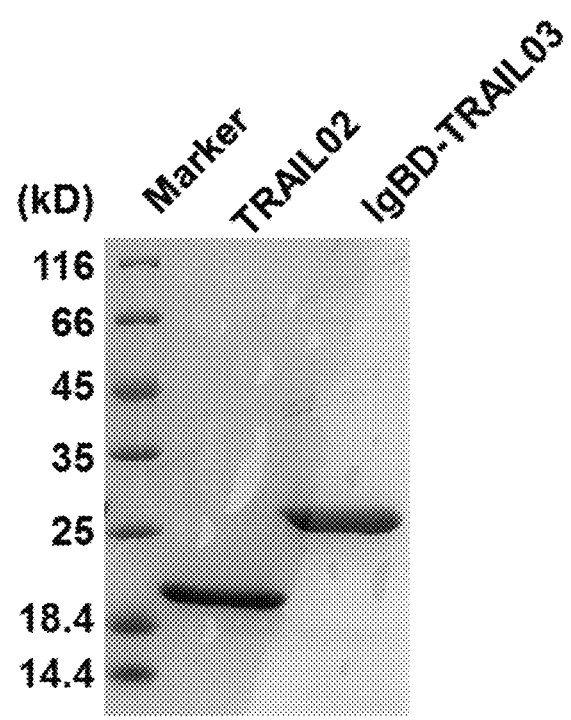
Figure 19:
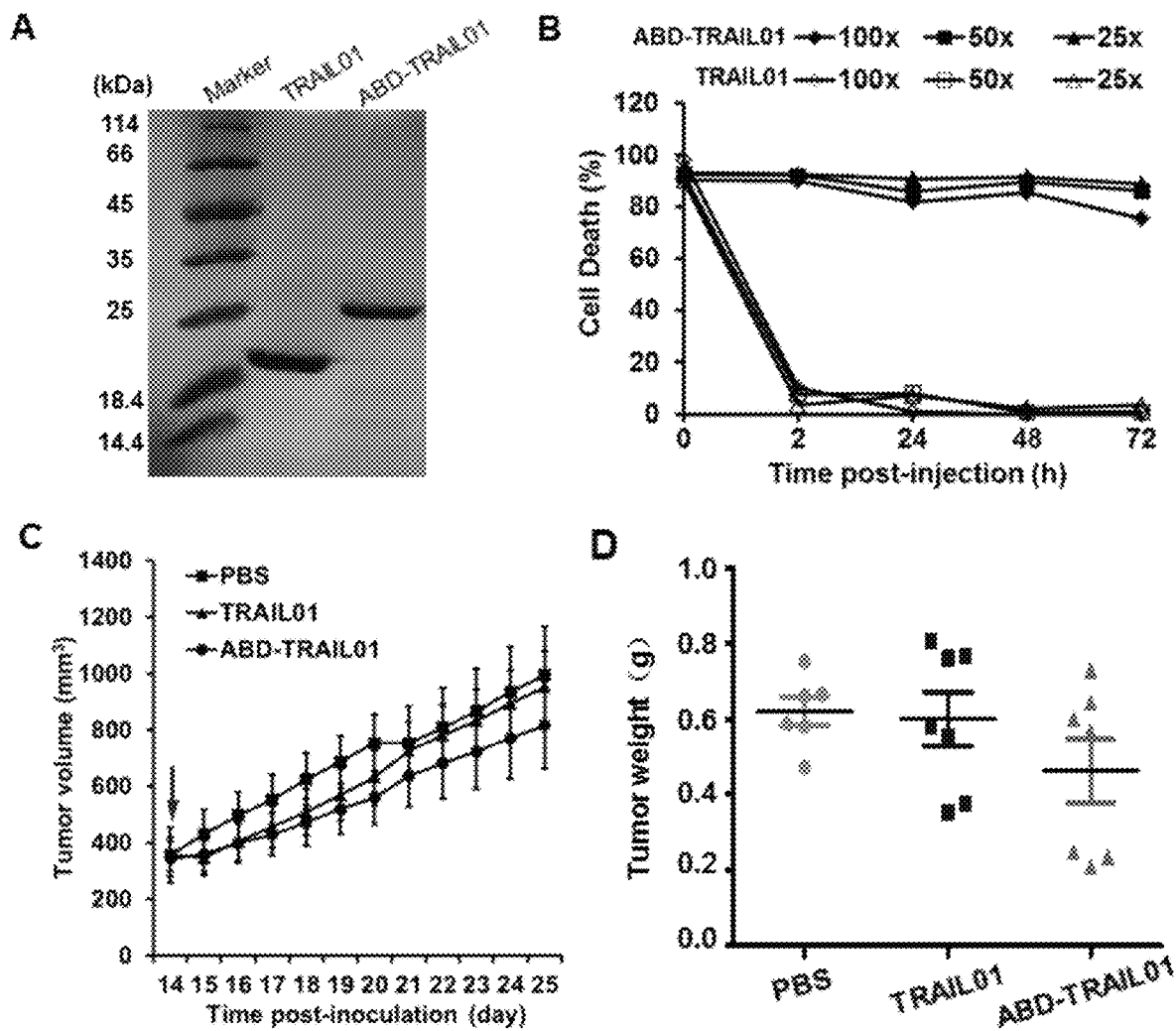
Figure 20:
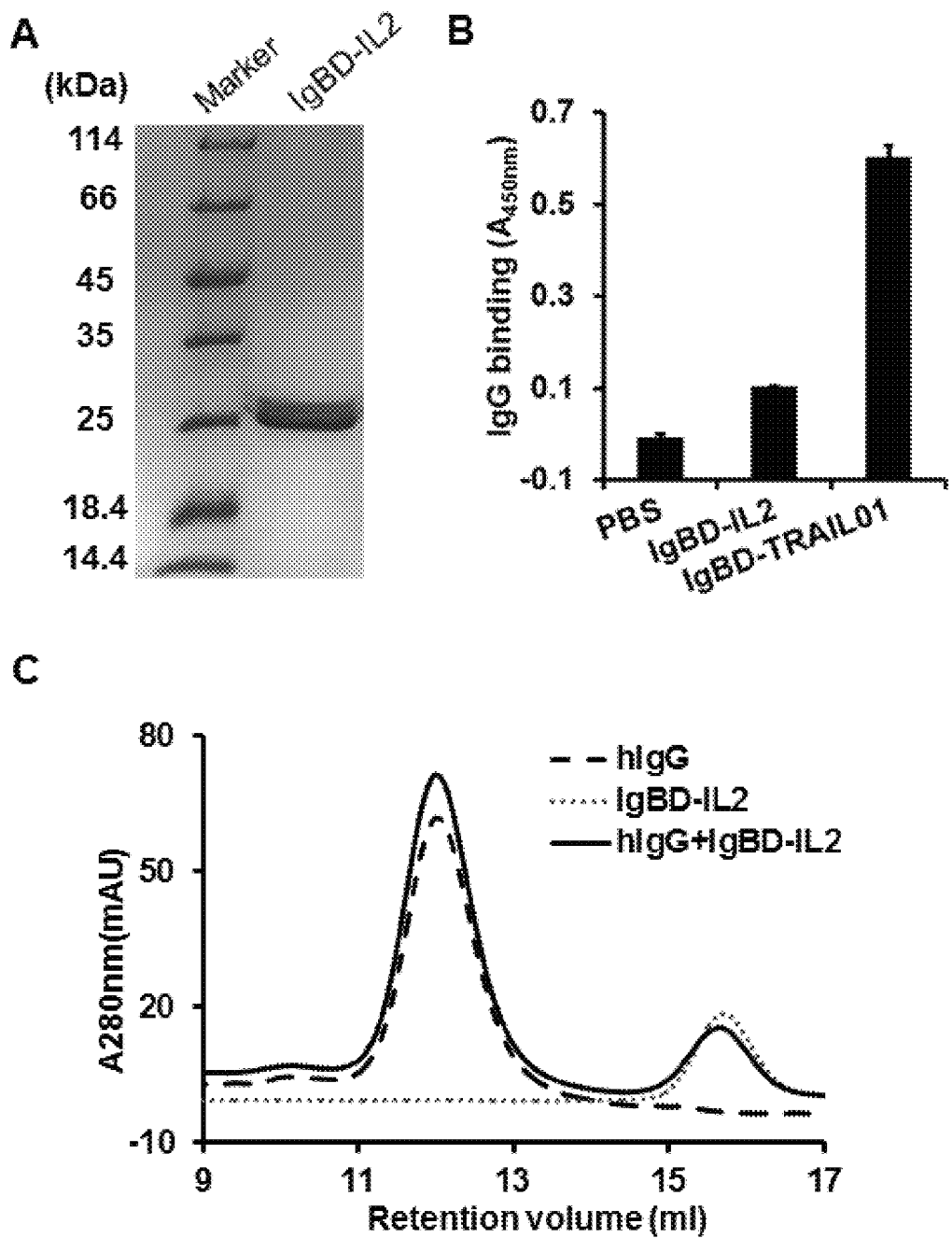

FIG. 11. Improvement of in vitro and in vivo antitumor effect of IgBD-TRAIL01 in LS174T tumor cells by binding to exogenous anti-EGFR antibody; (A) Expression of EGFR on the surface of LS174T tumor cells analyzed by flow cytometry; (B) The cytotoxicity of IgBD-TRAIL01 bound to or not to exogenous a-EGFR in LS174T tumor cells; (C) Growth curve of LS174T tumor grafts treated with IgBD-TRAIL01 bound to a-EGFR; the arrow indicates the administration time; (D) Weight of LS174T tumor grafts treated with IgBD-TRAIL01 bound to a-EGFR. The arrow indicates the administration time. ***: p<0.001;

FIG. 12. Improvement of in vitro and in vivo antitumor effect of IgBD-TRAIL01 in LS174T tumor cells by binding to exogenous anti-CD47 antibody (a-CD47); (A) Expression of CD47 on the surface of LS174T tumor cells measured by flow cytometry; (B) Cytotoxicity of IgBD-TRAIL01 bound to or not to exogenous a-CD47 in LS174T tumor cells; (C) Growth curve of LS174T tumor grafts treated with IgBD-TRAIL01 bound to exogenous a-CD47; the arrow indicates the administration time; (D) Weight of LS174T tumor grafts treated with IgBD-TRAIL01 bound to a-CD47. The arrow indicates the administration time. **: p<0.01;

FIG. 13. Gel electrophoresis of IgBD-TRAIL02 protein;

FIG. 14. Binding of IgBD-TRAIL02 to IgG;

FIG. 15. Binding of IgBD-TRAIL02 to death receptors DR4 and DR5 (A) and in vitro killing on tumor cells (B);

FIG. 16. In vivo pharmacokinetics of IgBD-TRAIL02 protein measured by $I^{131}$-labeling method (A) or cytotoxicity assays of residual proteins in blood collected at different time postinjection (B);

FIG. 17. In vivo Anti-tumor effect of IgBD-TRAIL02 bound to endogenous IgG; the arrow indicates the administration time. **: p<0.01;

FIG. 18. Gel electrophoresis of IgBD-TRAIL03 protein;

FIG. 19. The anti-tumor effect of ABD-TRAIL01; (A) Electrophoresis of ABD-TRAIL01 protein; (B) ABD-TRAIL01 pharmacokinetics determined by the cytotoxicity assay; (C, D) Growth curve (C) and tumor weight (D) of COLO205 tumor graft after ABD-TRAIL01 treatment; the arrow indicates the administration time;

FIG. 20. Analysis of the binding of IgBD-IL2 to IgG; (A) SDS-PAGE gel electrophoresis of IgBD-IL2; (B, C) ELISA (B) and size exclusion chromatography (C) analysis of the binding of IgBD-IL2 to IgG.

Figure 21:
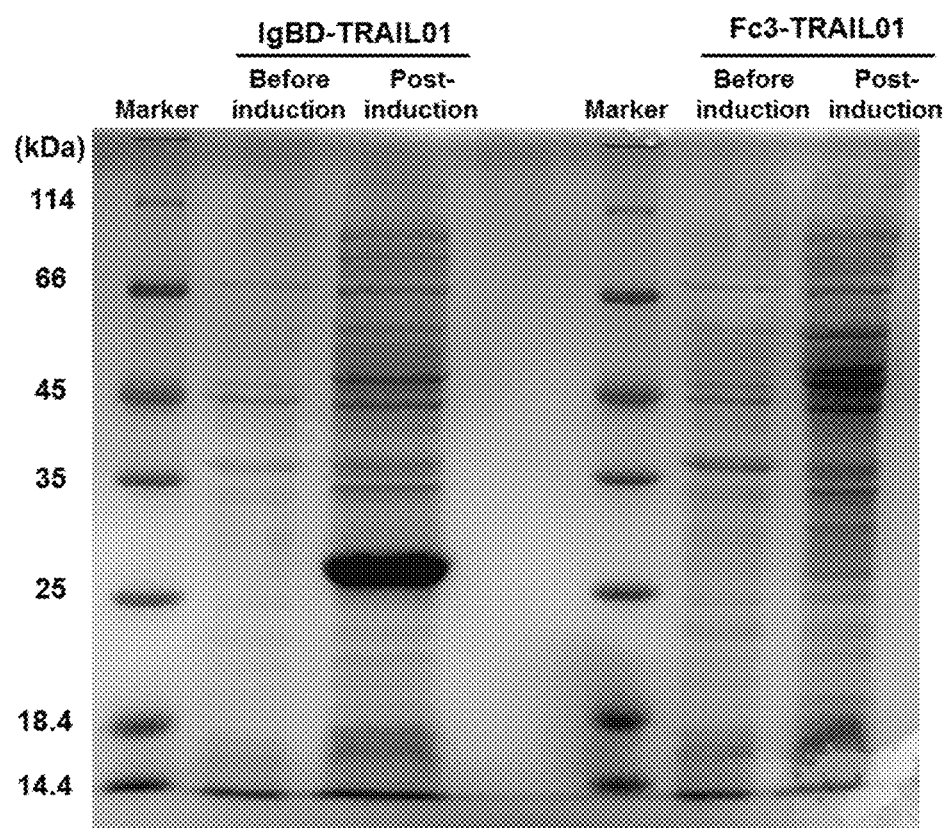

FIG. 21. Comparison of inducible expression of IgBD-TRAIL01 and Fc3-TRAIL01.

EXAMPLES

Example 1 Preparation of Fusion Protein IgBD-TRAIL01

1) Molecular Design and Gene Cloning of IgBD-TRAIL01

In order to construct IgG-binding TRAIL variants, IgG-binding domain (IgBD) was conjugated to N-terminus of TRAIL, and the resulting variant was named IgBD-TRAIL. First, the genes encoding IgBD01 and TRAIL01 were organized using software on computer according to the molecular design method to prepare the coding gene of the fusion protein IgBD-TRAIL01. Subsequently, the gene encoding IgBD-TRAIL01 was synthesized and cloned into pQE30 plasmid expression vector. The plasmid was designated as pQE30-IgBD-TRAIL01.

TRAIL01 nucleotide sequence:
(SEQ ID NO: 9)
5'-gtgagagaaagaggtcctcagagagtagcagctcacataactgggac cagaggaagaagcaacacattgtcttctccaaactccaagaatgaaaagg ctctgggccgcaaaataaactcctgggaatcatcaaggagtgggcattca ttcctgagcaacttgcacttgaggaatggcgaactggtcatccaagaaaa ggggttttactacatctattcccaaacatactttcgatttcaggaggaaa taaaagaaaacacaaagaacgacaaacaaatggtccaatatatttacaaa tacacaagttatcctgaccctatactgctgatgaaaagcgctagaaatag ttgttggtctaaagatgcagaatacggactctattccatctatcaagggg gattatttgagataagaaagatgacagaattttttgtttctgtaacaaatg agcacttgatagacatggaccatgaagccagcttttcggggccttttg gttggc-3'

IgBD01 nucleotide sequence:
(SEQ ID NO: 10)
5'-accacctacaagaggtgatcaacggcaagaccagaaaggcgagacca ccaccaaagcggttgacgcggagaccgcggcggcggcgttcgcgcagtac gcgcgtcgcaacggtgtggatggcgtttggacctatgacgatgcgaccaa gacctttaccgtgaccgaa-3'

(G4S)3 nucleotide sequence:
(SEQ ID NO: 12)
5'-ggcggaggcggttcaggcggaggtggctctggcggtggcggat ca-3'

IgBD-TRAIL01 nucleotide sequence:
(SEQ ID NO: 7)
5'-accacctacaagaggtgatcaacggcaagacctgaaaggcgagacc accaccaaagcggttgacgcggagaccgcggcggcggcgttcgcgcagta cgcgcgtcgcaacggtgtggatggcgtttggacctatgacgatgcgacca agacctttaccgtgaccgaaggcggaggcggttcaggcggaggtggactg gcggtggcggatcagtgagagaaagaggtcctcagagagtagcagctcac ataactgggaccagaggaagaagcaacacattgtcttaccaaactccaag aatgaaaaggctctgggccgcaaaataaactcctgggaatcatcaaggag tgggcattcattcctgagcaacttgcacttgaggaatggcgaactggtca tccaagaaaaggggttttactacatctattcccaaacatactttcgattt caggaggaaataaaagaaaacacaaagaacgacaaacaaatggtccaata tatttacaaatacacaagttatcctgaccctatactgctgatgaaaagcg ctagaaatagttgttggtctaaagatgcagaatacggactctattccatc tatcaaggggattatttgagcttaagaaagatgacagaattttttgtttc tgtaacaaatgagcacttgatagacatggaccatgaagccagcttatcgg ggccttttggttggc-3'

2) Expression and Purification of the Fusion Protein IgBD-TRAIL01

Figure 1:
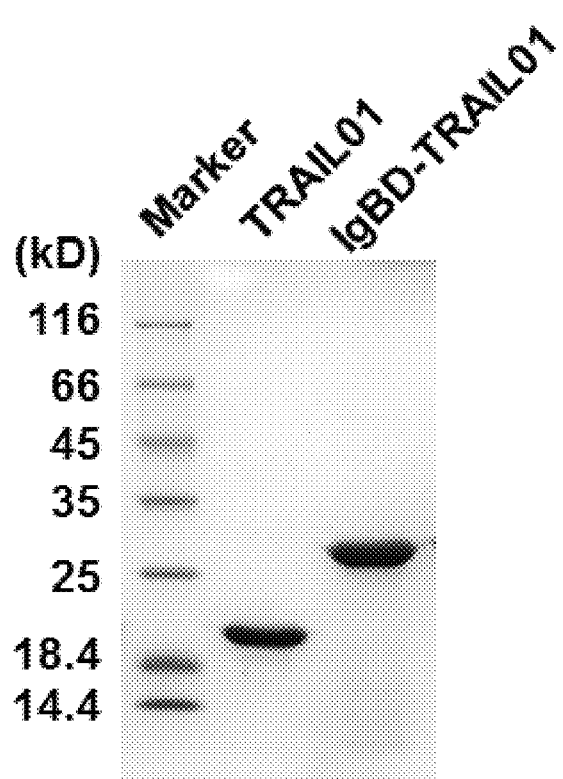
FIG. 1. Gel electrophoresis of IgBD-TRAIL01.

According to the conventional method of molecular biology, the plasmid pQE30-IgBD-TRAIL01 was introduced into E. coli M15 cells. The transfected cells were incubated in LB liquid medium (containing 100 μg/ml ampicillin and 30 μg/ml kanamycin) at 37° C. to logarithmic growth phase. Subsequently, isopropyl thiogalactoside (IPTG, 0.05-1 mM) was added into the E. coli cells to induce the expression of IgBD-TRAIL01. After overnight culture at low temperature (20-25° C.), all bacteria were collected by centrifugation and resuspended in lysis buffer (50 mM phosphate, pH 8.0, 300 mM NaCl, 10 mM β-mecaptoethanol, 1 mM phenylmethylsulfonylfluoride, and 5 mM imidazole), and then broken in a high-pressure homogenizer (80-100 MPa) for 4-5 processes. The recombinant protein in the supernatant was purified by Ni-NTA affinity chromatography and detected by gel electrophoresis. As shown in FIG. 1, as expected, the molecular weight of purified IgBD-TRAIL01 is about 28 KD, compared to 20 KD of TRAIL01. The purified IgBD-TRAIL01 protein was shown as a single band on the gel, indicating that the IgBD-TRAIL01 was purified to homogeneity.

```
TRAIL01 amino acid sequence:
                                          (SEQ ID NO: 1)
NH2-VRERGPQRVAAHITGTRGRSNTLSSPNSKNEKALGRKINSWESSRS

GHSFLSNLHLRNGELVIQEKGFYYTYSQTYFRFQEEIKENTKNDKQMVQY

IYKYTSYPDPILLMKSARNSCWSKDAEYGLYSIYQGGLFELKKDDRIFVS

VTNEHLIDMDHEASFFGAFLVG-COOH

IgBD01 amino acid sequence:
                                          (SEQ ID NO: 2)
NH2-TTYKLVINGKTLKGETTTKAVDAETAAAAFAQYARRNGVDGVWTYD

DATKTFTVTE-COOH (G4S)3 amino acid sequence:
                                          (SEQ ID NO: 4)
NH2-GGGGSGGGGSGGGGS-COOH IgBD-TRAIL01 amino acid sequence:
                                          (SEQ ID NO: 5)
NH2-TTYKLVINGKTLKGETTTKAVDAETAAAAFAQYARRNGVDGVWTYD

DATKTFTVTEGGGGSGGGGSGGGGSVRERGPQRVAAHITGTRGRSNTLSS

PNSKNEKALGRKINSWESSRSGHSFLSNLHLRNGELVIQEKGFYYTYSQT

YFRFQEEIKENTKNDKQMVQYIYKYTSYPDPILLMKSARNSCWSKDAEYG

LYSIYQGGLFELKKDDRIFVSVTNEHLIDMDHEASFFGAFLVG-COOH
```

Example 2 Binding of Fusion Protein IgBD-TRAIL01 to IgG

IgBD01 alone can bind to IgG. However, there may be possible interactions between the various domains consisting of the fusion protein, that may have a negative impact on their functions. After fusion to TRAIL01, it was not sure that the IgBD01 can be fully exposed to exert IgG-binding. Therefore, it is necessary to determine IgG-binding ability of the fusion protein IgBD-TRAIL01. ELISA and size exclusion chromatography were used to detect the IgG-binding of IgBD-TRAIL01.

1) ELISA Human IgG (hIgG) or mouse IgG (mIgG) was coated in a well plate for ELISA. IgBD-TRAIL01 protein was diluted with phosphate buffered saline (PBS, 10 mM $Na_2HPO_4$, 2.68 mM KCl, 2 mM $KH_2PO_4$, 500 mM NaCl, 1% BSA) to a final concentration of 0.05-2.5 nM followed by addition into the wells coated with IgG at 100 l/well. After incubating at 37° C. for 1 h, excess protein was removed. The wells were washed 3 times with PBS followed by addition of biotin-labeled anti-TRAIL antibody. After 1 h incubation, horseradish peroxidase (HRP)-labeled streptavidin and its substrate were added into the well followed by measuring A450 reflecting the IgG-binding of IgBD-TRAIL01. TRAIL01 protein was used as a control to determine whether IgBD-TRAIL01 bound to IgG.

Figure 2:
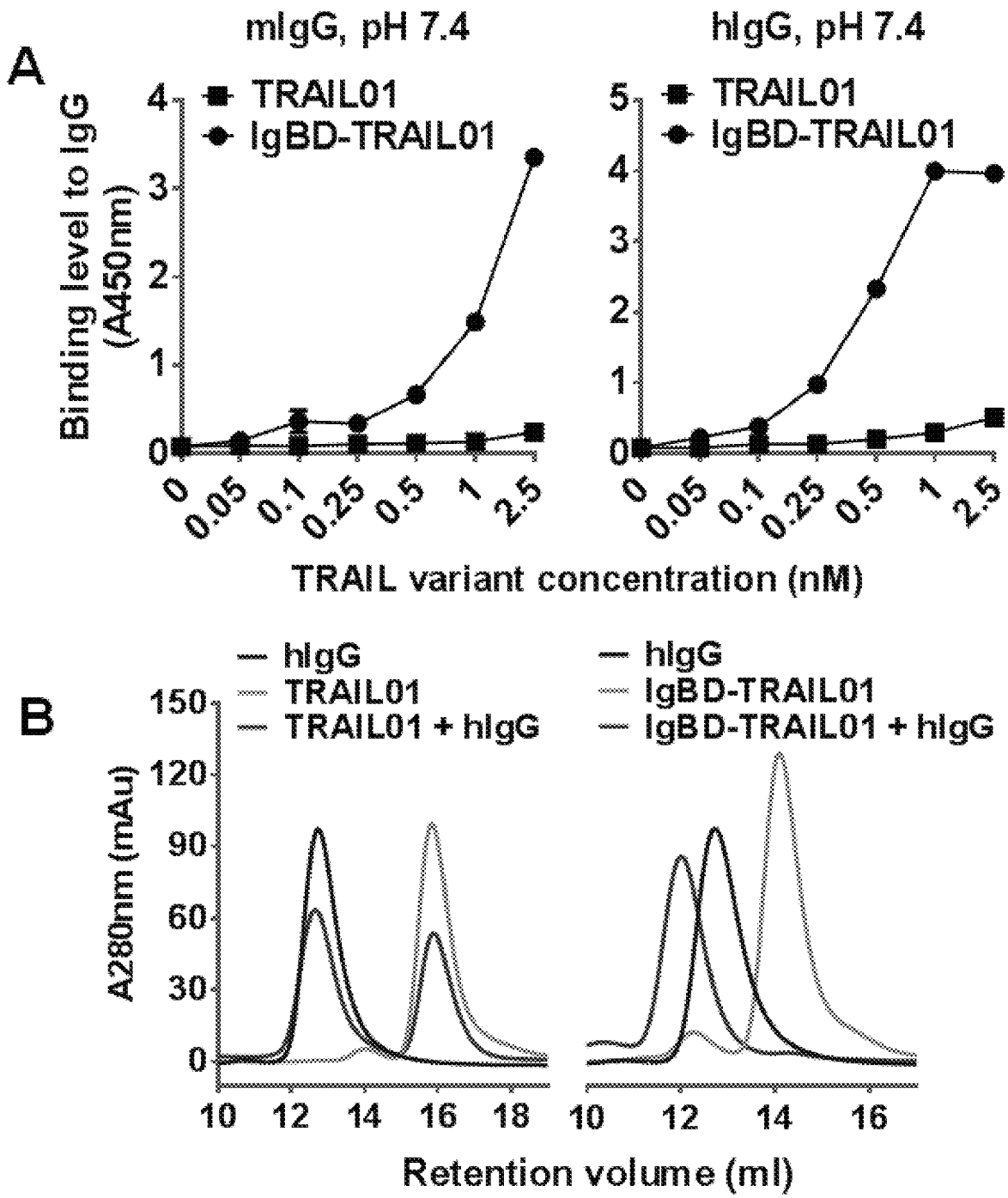
FIG. 2. The binding of IgBD-TRAIL01 to IgG measured by ELISA assay (A) and size exclusion chromatography (B)

As shown in FIG. 2A, after incubation with either mIgG or hIgG, A450 nm values of IgBD-TRAIL01 group increased with increasing of protein concentration. However, the A450 nm values of TRAIL01 group did not change with the increasing of protein concentration. This results indicated that TRAIL01 cannot bind IgG, while IgBD-TRAIL01 can bind both mIgG and hIgG. These facts suggest that fusion of IgBD01 to the N-terminus of TRAIL01 endows TRAIL01 with IgG-binding ability.

2) Size exclusion chromatography If IgBD-TRAIL01 could bind IgG, a novel complex that is larger than individual IgBD-TRAIL01 and IgG would be detected by size exclusion chromatography. To examine the IgG-binding, IgBD-TRAIL01 was incubated with hIgG at a molar ratio of 1:1 for 30 min at room temperature followed by analysis of the mixture using a gel filtration column Superdex 200 10/30 pre-equilibrated with PBS. TRAIL01 was used as a control.

As shown in FIG. 2B, after TRAIL01 and hIgG were mixed at a molar ratio of 1:1, two protein peaks with retention volumes of 12.7 ml and 16.0 ml representing hIgG and TRAIL01 appeared on the gel filtration column, indicating that TRAIL01 did not bind hIgG. However, after IgBD-TRAIL01 was incubated with hIgG, only a single protein peak with the retention volume of 12.0 ml, which is smaller than the retention volumes of individual hIgG (12.7 ml) and IgBD-TRAIL01 (15.8 ml), indicating that IgBD-TRAIL01 can bind hIgG to form a novel complex. These results demonstrate that IgBD-TRAIL01, but not TRAIL01, can bind IgG, and fusing IgBD01 to the N-terminus of TRAIL01 endows TRAIL01 with IgG-binding ability.

Example 3 Binding of Fusion Protein IgBD-TRAIL01 to Death Receptors

Figure 3:
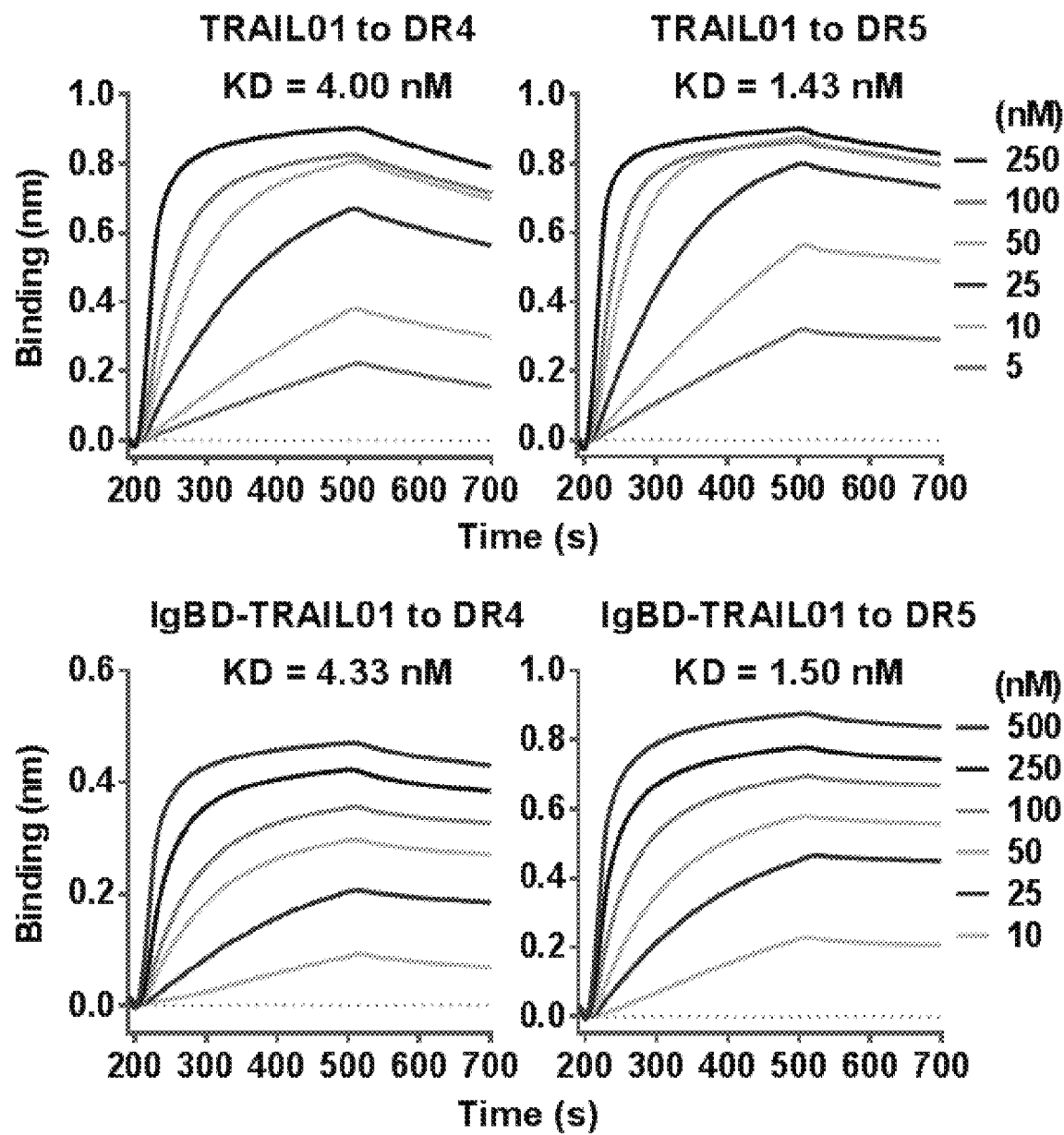
FIG. 3. Binding of IgBD-TRAIL01 to death receptors DR4 and DR5.

TRAIL induced apoptosis of tumor cells by binding to death receptors DR4 and DR5, which is related to its anti-tumor effect. To measure the death receptor binding of IgBD-TRAIL01 by biolayer interferometry (BLI), the death receptor fusion protein DR4-Fc or DR5-Fc was trapped to the protein A-coated probe followed by insertion into the solution containing different concentrations of IgBD-TRAIL01 protein to bind for 300 s, and disassociation in PBS for 200 s. The binding constant Ka and the dissociation constant Kd were determined, and then the affinity KD was calculated according to the formula (KD=Kd/Ka). As shown in FIG. 3, the affinities of IgBD-TRAIL01 and TRAIL01 to DR4 are 4.33 nM and 4.00 nM, respectively, and their affinities to DR5 are 1.43 nM and 1.50 nM, respectively. The similarity between IgBD-TRAIL01 and TRAIL01 in death receptor-binding demonstrate that fusing IgBD01 to the N-terminus of TRAIL01 did not interfere with the binding of TRAIL01 to the death receptors.

Example 4 In Vitro Cytotoxicity of Fusion Protein IgBD-TRAIL01

Figure 4:
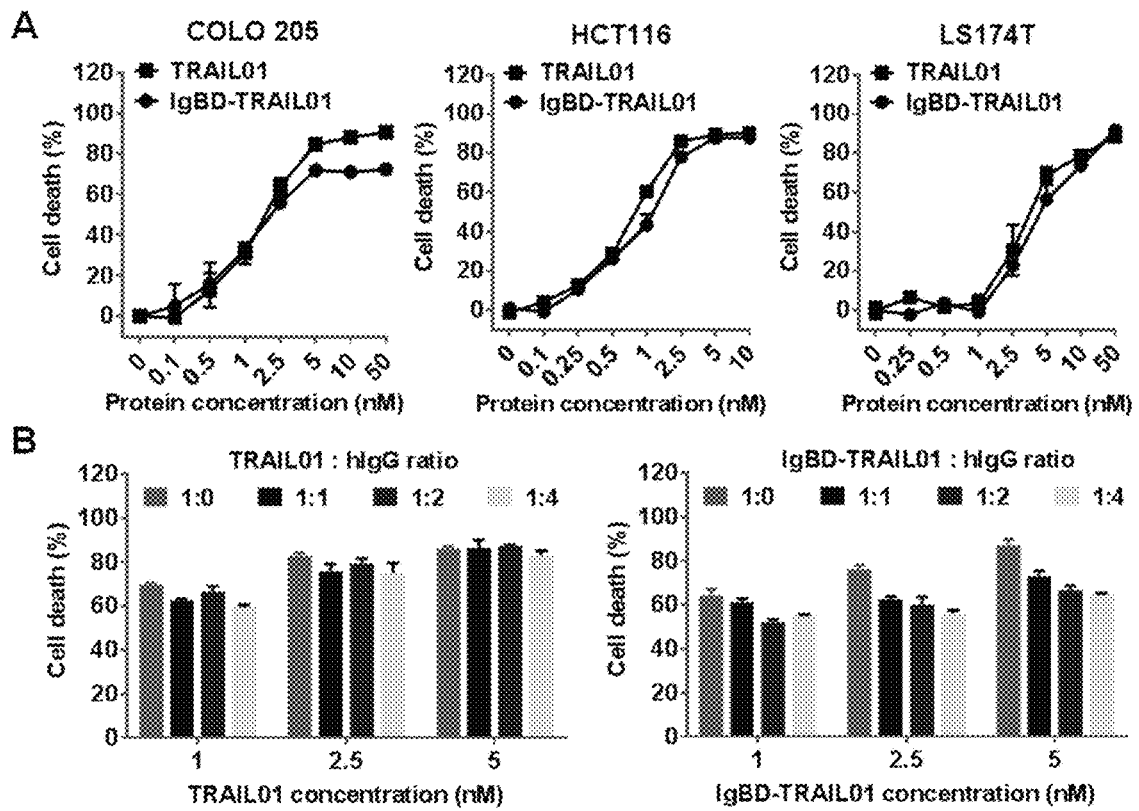
FIG. 4. In vitro cytotoxicity of IgBD-TRAIL01 in tumor cells; (A) Comparison of cytotoxicity of IgBD-TRAIL01 and TRAIL in serum-free medium; (B) Comparison of cytotoxicity of IgBD-TRAIL01 protein after incubated with IgG at different ratios of protein and IgG.

TRAIL01 could induce apoptosis of tumor cells. IgBD fusion might reduce the cytotoxicity of TRAIL01. To determine the influence, the cytotoxicity of IgBD-TRAIL01 was measured in serum-free medium and compared with that of TRAIL01. As shown in FIG. 4A, IgBD-TRAIL01 is similar to TRAIL01 in cytotoxicities in three tumor cells including COLO205, HCT116, and LS174T, indicating that IgBD01 fusion did not reduce the cytotoxicity of TRAIL01 in tumor cells. However, as IgBD-TRAIL01 could bind to hIgG, the bound hIgG might exert steric hindrance and affect the cytotoxicity of TRAIL01. Consequently, we further compared the cytotoxicities of IgBD-TRAIL01 in tumor cells after preincubation with and without hIgG for 30 min at room temperature. As shown in FIG. 4B, the cell death rate induced by IgBD-TRAIL01 was slightly reduced along the increasing of the concentration of hIgG, indicating that the bound hIgG had little impact on the cytotoxicity of IgBD-TRAIL01 in tumor cells.

Figure 5:
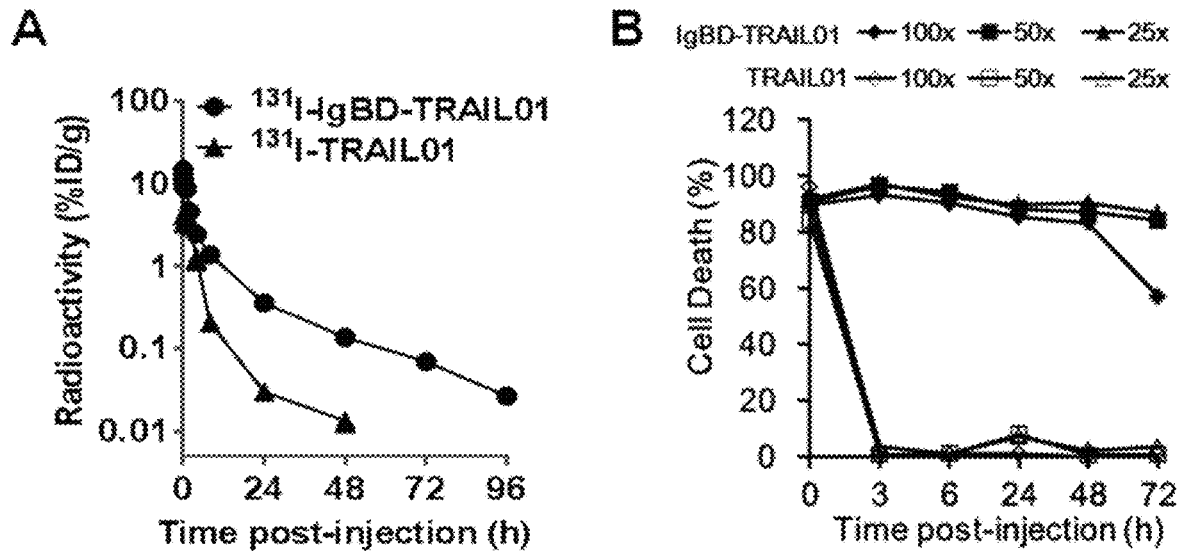
FIG. 5. In vivo pharmacokinetics of IgBD-TRAIL01 measured by $I^{131}$-labeling method (A) and cytotoxicity assays (B)

Example 5 Binding to Endogenous IgG Extends the In Vivo Half-Life of IgBD-TRAIL01 Fusion Protein IgG with large molecular weight showed a long half-life in vivo. Once enter the bloodstream, IgBD-TRAIL01 might bind to endogenous IgG, which might prolong its half-life in vivo. To monitor the metabolism of this protein in vivo, The protein was labeled with radioisotope $I^{131}$ under catalysis with N-bromosuccinimide. After injection of the protein into the mouse by the tail vein, the blood was collected at different time points (1 min-96 h) for measuring the radiation dose in the blood. Simultaneously, to verify the presence of TRAIL01, the cytotoxicity of residual proteins in the blood was measured in tumor cells after the plasma was diluted by different times (25-100 times). As shown in FIGS. 5A and 5B, $I^{131}$-labeled TRAIL01 and IgBD-TRAIL01 injected in the mice showed time-depend decrease in residual radiation and cytotoxicity. However, the IgBD-TRAIL01 was cleared slower than TRAIL01 from the blood. The half-life of TRAIL01 was only about 15 min, whereas the half-life of IgBD-TRAIL01 was as long as 16 h. These results indicated that once enter the blood, IgBD-TRAIL01 could bind to endogenous IgG to exert prolonged half-life that was 50-60 folds that of TRAIL01.

Example 6 Binding to Endogenous IgG Increases the Tumor Uptake of IgBD-TRAIL1 Fusion Protein The half-life of IgBD-TRAIL01 was obviously longer than that of TRAIL01, suggesting that the tumor uptake of IgBD-TRAIL01 might be higher than that of TRAIL01. The tumor uptake of IgBD-TRAIL01 was investigated using optical imaging and radioisotope-tracing technology and compared to that of TRAIL01.

Figure 6:
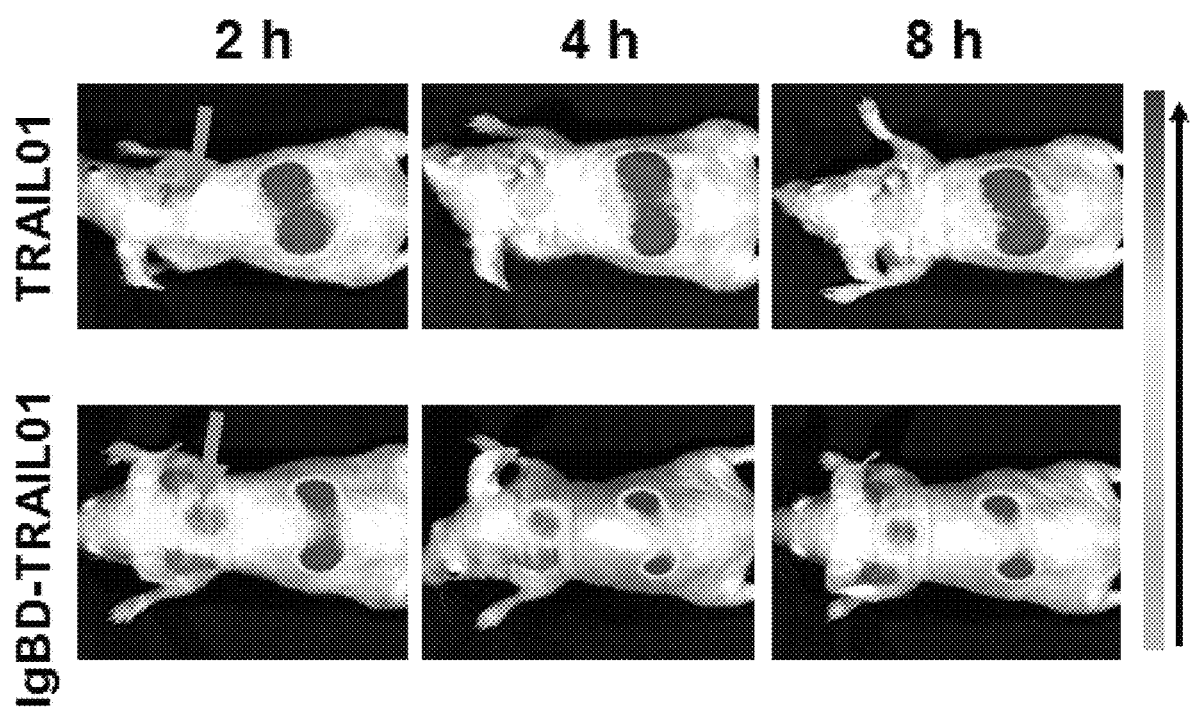
FIG. 6. Tumor uptake of IgBD-TRAIL01 monitored by in vivo optical imaging (Tumor was indicated by arrow)

1) Measurement by Optical imaging: To monitor the tumor uptake of IgBD-TRAIL01, the protein was firstly labeled with near-infrared dye CF750 followed by injection into the tumor-bearing mice through the tail vein. The mice were anesthetized at different times and scanned with IVIS optical imaging system. Time-dependent change of fluorescence in the tumor reflected the tumor uptake of protein. As shown in FIG. 6, During the period of 2~8 h postinjection, the content of IgBD-TRAIL01 in COLO205 tumor grafts was higher than that of TRAIL01, indicating that the tumor uptake of IgBD-TRAIL01 was higher than that of TRAIL01.

Figure 7:
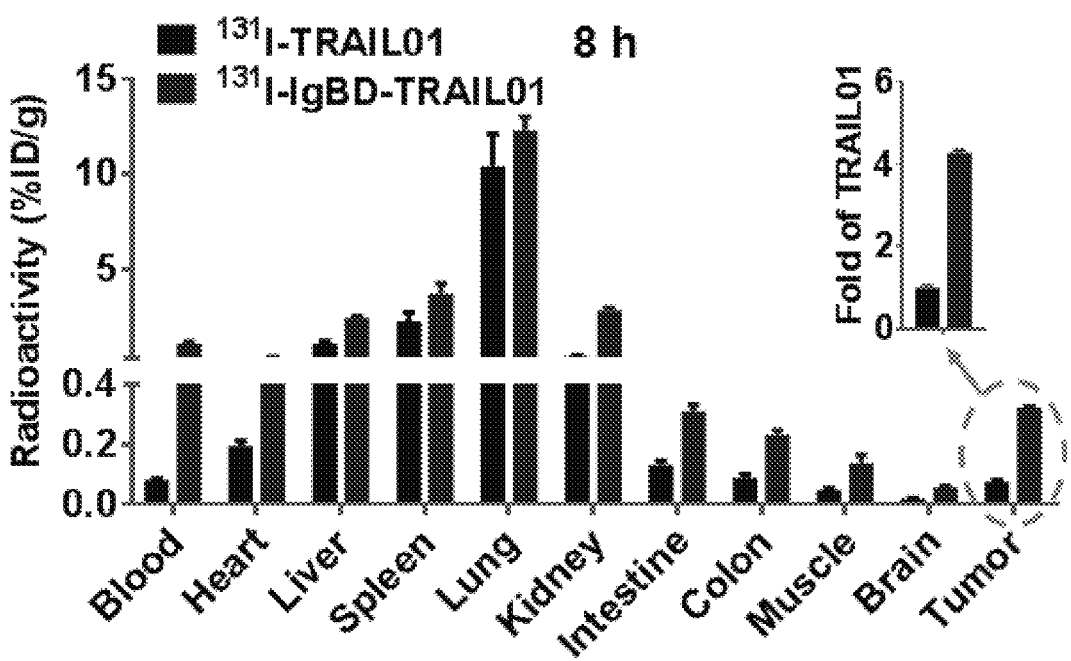
FIG. 7. Tumor uptake of IgBD-TRAIL01 measured by $I^{131}$-labeling method at 8 h (A) or 24 h (B) postinjection.
Figure 7:
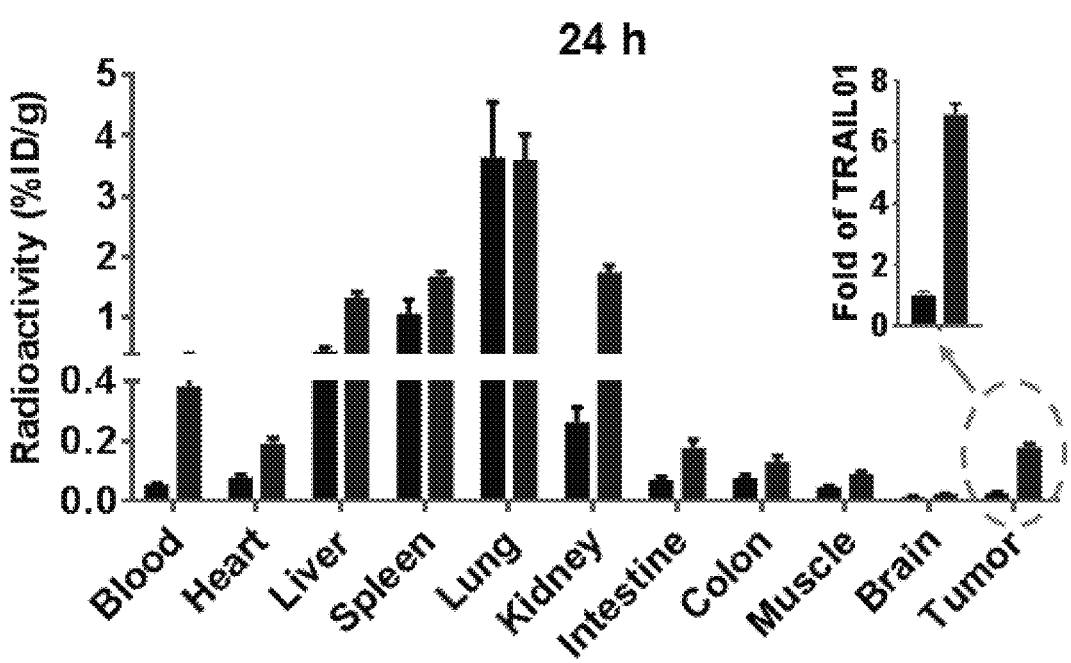

2) Measurement by Radioisotope-tracing method: To monitor the tumor uptake of IgBD-TRAIL01, the protein was labeled with radioisotope $I^{131}$ prior to injection into mice bearing COLO 205 tumor grafts. To measure the protein in the tumor and other tissues, the mice were sacrificed at 8 h and 24 h postinjection, respectively, As shown in FIG. 7, the content of IgBD-TRAIL01 in the tumor was about 4-7 times higher than that of TRAIL01 during 8-24 h postinjection, indicating that tumor uptake of IgBD-TRAIL01 was significantly higher than that of TRAIL01. Accordingly, the amount of IgBD-TRAIL01 in other tissues was also higher than that of TRAIL01 at various degrees, suggesting that prolonging the half-life widely improved the tissue distribution of IgBD-TRAIL01.

Example 7 Binding to Endogenous IgG Improves the In Vivo Antitumor Effect of IgBD-TRAIL01 Fusion Protein Once enter the blood, IgBD-TRAIL01 binds to endogenous IgG to exert prolonged half life, which might improve the antitumor effect of the protein. The anti-tumor effect of IgBD-TRAIL01 bound to endogenous IgG was evaluated in mice bearing COLO205, LS174T or HCT116 tumor grafts. To construct the animal model, tumor cells (1~2×10$^6$ cells) were subcutaneously injected into the mice at the back neck. Once the tumor grafts were palpable, the length (L) and the width (W) of the tumor grafts were measured every day, and the tumor volume (V) was calculated according to the formula V=L×W$^2$/2.

Figure 8:
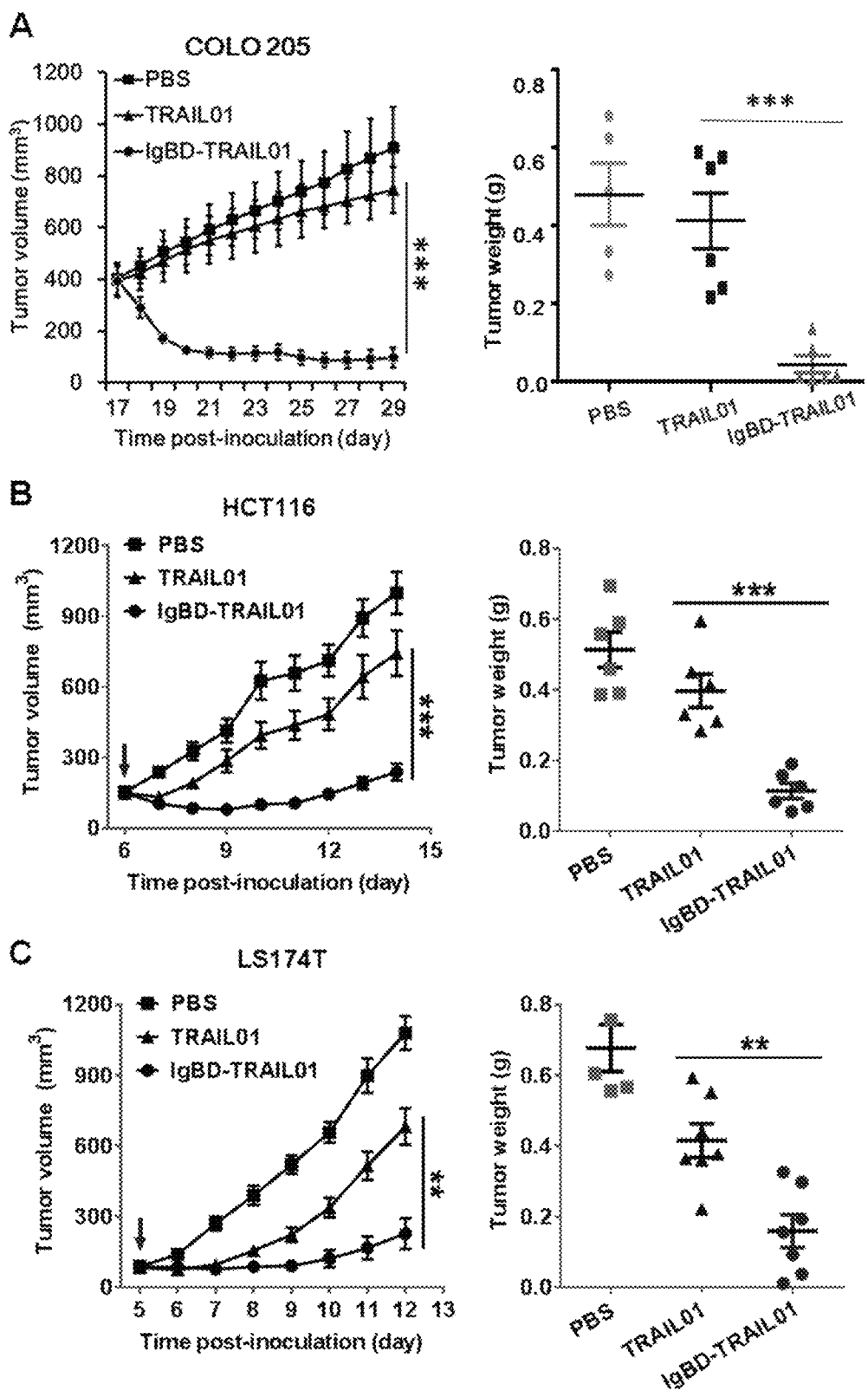
FIG. 8. In vivo anti-tumor effect of IgBD-TRAIL01 bound to endogenous IgG; the arrow indicates the administration time. *: $p<0.001$; : $p<0.01$.

When the average tumor volume reached about 400 mm$^3$ in mice bearing COLO205 tumor grafts, the mice were randomly divided into three groups (N=5-6 mice) followed by treatment with IgBD-TRAIL01 or TRAIL01 at 0.5 mg/kg. The control group was treated with the same volume of PBS. As shown in FIG. 8A. TRAIL01 exerted little tumor growth suppression when the protein was administered on the 17$^{th}$ day after inoculation. However, after treatment with the same amount of IgBD-TRAIL01, the tumor grafts shrink and became white on the next day. All tumor volume drastically decreased within 4-5 days after administration and the little tumor growth was observed during the continuous observation. At the end of the observation, the tumor volumes in PBS, TRAIL01 and IgBD-TRAIL01-treated mice were 908±157.5 mm$^3$, 745±90.6 mm$^3$ and 96±38.0 mm$^3$, respectively, and the corresponding average tumor weights were 0.48±0.18 g, 0.41±0.17 g and 0.04±0.03 g, respectively. These results demonstrated that the tumor grafts in mice treated with IgBD-TRAIL01 were significantly (p<0.001) smaller than that of tumor grafts in mice treated with TRAIL01. In mice bearing LS174T tumor grafts, the mice were randomly divided into 3 groups (N=7) when the average tumor volume reached about 100 mm$^3$ followed by treatment with IgBD-TRAIL01 or TRAIL01 at 5 mg/kg. PBS was used as control. After treatment, the tumor was measured every day. As shown in FIG. 8B. TRAIL01 could inhibit the tumor growth. However, the tumor growth rate in IgBD-TRAIL01 treatment group was significantly slower than that in TRAIL01 treatment group. At the end of the observation, the tumor volumes in PBS, TRAIL01 and IgBD-TRAIL-treated mice were 1081.4±72.2 mm$^3$, 683.6±77.1 mm$^3$, 228.9±65.8 mm$^3$, respectively, and the corresponding average tumor weights were 0.68±0.07 g, 0.42±0.05 g, 0.16±0.05 g, respectively. These results demonstrated that the tumor grafts in mice treated with IgBD-TRAIL01 were significantly (p<0.001) smaller than that in mice treated with TRAIL01.

In mice bearing HCT116 tumor grafts, the mice were randomly divided into 3 groups (N=6) and treated with 5 mg/kg IgBD-TRAIL01 or TRAIL01 when the average tumor volume reached about 150 mm$^3$. The mice in the control group was treated with PBS. After treatment, the size of the tumor was measured every day. As shown in FIG. 8C, the tumor growth rate in TRAIL01-treated mice was slower than that in PBS group. However, the tumor growth in IgBD-TRAIL01-treated mice was much slower than that in TRAIL01-treated mice. At the end of the observation, the tumor volumes in PBS, TRAIL01 and IgBD-TRAIL01-treated mice were 1000.1±89.3 mm$^3$, 743.4±96.8 mm$^3$, and 238.4±35.6 mm$^3$, respectively, and the corresponding tumor weights were 0.51±0.05 g, 0.40±0.05 g, and 0.11±0.02 g, respectively. These results demonstrated that the tumor grafts in IgBD-TRAIL01-treated mice were obviously ($p<0.01$) smaller than that in TRAIL01-treated mice.

Above results indicated that the antitumor effect of IgBD-TRAIL01 bound to endogenous IgG antibody was much better than that of TRAIL01 that could not bound to endogenous IgG antibody in three animal model bearing tumor grafts. IgBD fusion significantly enhanced the antitumor effect of TRAIL01.

Figure 9:
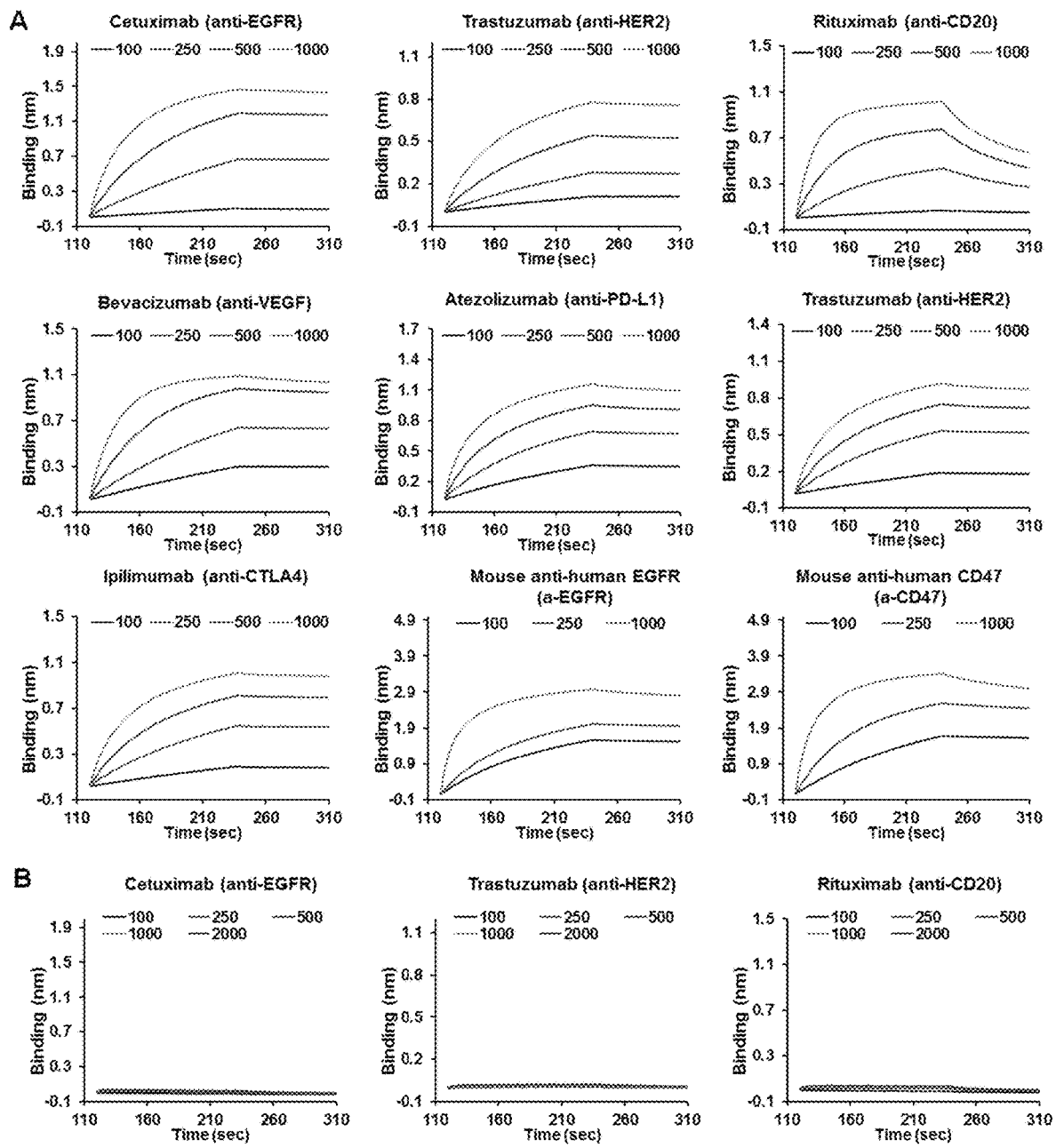
FIG. 9. Binding of IgBD-TRAIL01 (A) and TRAIL01 (B) to exogenous antibodies.

Example 8 Binding of IgBD-TRAIL01 Fusion Protein to Exogenous Antigen-Specific IgG Antibody In addition to binding to endogenous IgG, IgBD-TRAIL01 can also bind to exogenous antigen-specific IgG antibodies. In order to detect the binding of IgBD-TRAIL01 to exogenous antibody, the antibody was first immobilized on the protein A-coated probe. Subsequently, the probe was inserted into a solution containing different concentrations of IgBD-TRAIL01 for association followed by disassociation in PBS. The association (ka) and dissociation (kd) constants were measured, and the affinity (KD) was calculated according to the formula (KD=kd/ka). The same concentration of TRAIL01 was used as a control. As shown in FIG. 9A, IgBD-TRAIL01 showed strong binding to various antibodies (FIG. 9A). These antibodies included human antibodies such as Cetuximab (anti-EGFR), Trastuzumab (anti-HER2), Rituximab (anti-CD20), Bevacizumab (anti-VEGF), Atezolizumab (anti-PD-L1), Nivolumab (anti-PD1), Ipilimumab (anti-CTLA4), murine antibodies against EGFR (a-EGFR) or CD47 (a-CD47). The affinity of IgBD-TRAIL01 for these antibodies are all at nM levels. However, TRAIL01 did not bind to tested antibodies (FIG. 9B), indicating that the fused IgBD of the present invention endowed TRAIL01 with exogenous IgG antibody-binding ability.

Example 9 Binding to Exogenous Antigen-Specific IgG Antibody Enhances the In Vivo Anti-Tumor Effect of Fusion Protein IgBD-TRAIL01 by Improving its Tumor Targeting Many antigens are highly expressed on the surface of tumor cells. For example, Epidermal Growth Factor Receptor (EGFR) was highly expressed on the surface of colorectal cancer cells. Anti-EGFR IgG antibody (a-EGFR, purchased from Bio X Cell Inc.) could bind to tumor cells by recognizing EGFR. If IgBD-TRAIL01 could bind to a-EGFR, the binding of TRAIL01 to tumor cells could be increased and its cytotoxicity should be enhanced.

Figure 10:
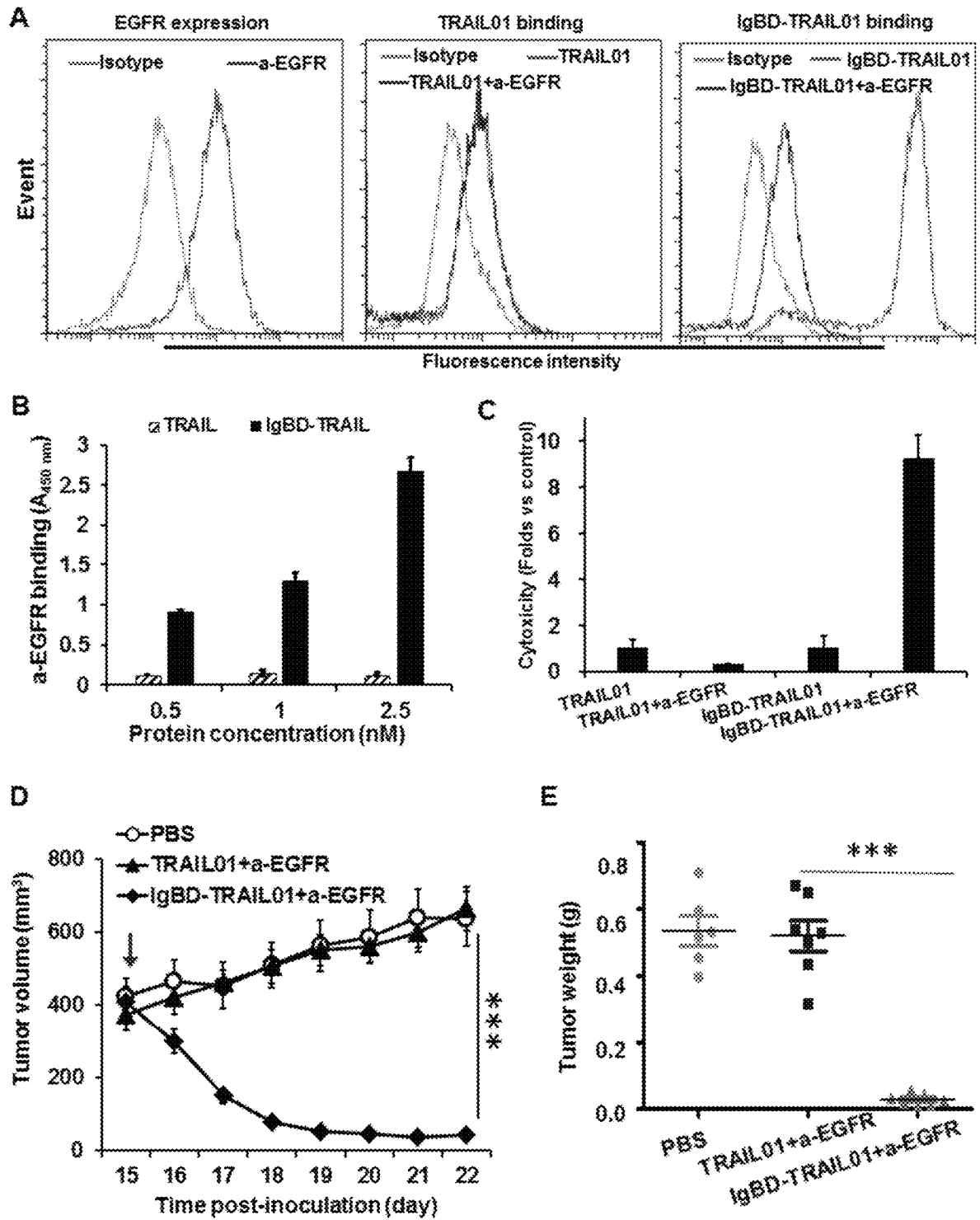
FIG. 10. Improvement of in vitro and in vivo antitumor effect of IgBD-TRAIL01 in COLO205 tumor cells by binding to exogenous anti-EGFR antibody (a-EGFR); (A) Expression of EGFR on the surface of COLO205 tumor cells. And the a-EGFR-mediated binding of IgBD-TRAIL01 or TRAIL01 to COLO205 tumor cells; (B) Analysis of the binding of IgBD-TRAIL01 and TRAIL01 to a-EGFR by ELISA; (C) Cytotoxicity of IgBD-TRAIL01 in COLO205 tumor cells before and after binding to a-EGFR; (D) Growth curve of COLO205 tumor grafts treated with IgBD-TRAIL01 bound to a-EGFR; (E) Weight of COLO205 tumor after treatment with IgBD-TRAIL1 bound to a-EGFR. The arrow indicates the administration time. ***: p<0.001.

To examine the antibody-mediated cell binding, IgBD-TRAIL01 labeled with fluorescent dye was mixed with a-EGFR antibody and incubated with the cells prior to analysis using flow cytometry. As shown in FIG. 10A, EGFR was highly expressed on the surface of COLO 205 colorectal cancer cells. Compared with IgBD-TRAIL01, IgBD-TRAIL01 bound to a-EGFR antibody exerted higher binding to tumor cells. However, incubation with a-EGFR antibody did not enhance the binding of TRAIL01 to tumor cells. These results indicated that binding to the antigen-specific exogenous antibody enhanced the binding of IgBD-TRAIL01 to tumor cells. ELISA analysis further proved that IgBD-TRAIL01, but not TRAIL01, could bind to a-EGFR antibody (FIG. 10B). After binding to a-EGFR antibody, IgBD-TRAIL01 exerted 8-10 times higher cytotoxicity in COLO205 tumor cells (FIG. 10C). However, incubation with antibody did not increase the cytotoxicity of TRAIL01 in COLO205 tumor cells. These results indicated that the IgBD fusion endowed TRAIL01 with a-EGFR antibody-binding ability, thus improving its cell binding and cytotoxicity in EGFR-expressing tumor cells.

To test the impact of exogenous antigen-specific antibody on the antitumor effect of IgBD-TRAIL01, IgBD-TRAIL01 (1 mg/kg) was mixed with a-EGFR at a molar ratio of 1.1 (IgBD-TRAIL01+ a-EGFR) and incubated at room temperature for 30 min prior to injection into mice bearing COLO 205 tumor grafts. The mice in control group were injected with the mixture of the same amount of TRAIL01 and a-EGFR (TRAIL01+ a-EGFR) or an equal volume of PBS. The tumor volume was measured every day. As shown in FIG. 10D, after injection of IgBD-TRAIL01+a-EGFR, the tumor size rapidly decrease. However, injection of the same dose of TRAIL01+a-EGFR mixture did not show obvious suppression on tumor growth. At the end of the observation, the tumor volumes of mice treated with PBS, TRAIL01+a-EGFR, or IgBD-TRAIL01+a-EGFR were 638±74.4 mm$^3$, 664±61.5 mm$^3$, and 42±7.4 mm$^3$, respectively. The tumor weights corresponding to these three groups were 0.5±0.02 g, 0.52±0.04 g, and 0.03±0.01 g, respectively (FIG. 10E). The tumors treated with IgBD-TRAIL01+a-EGFR were significantly ($p<0.001$) smaller than those treated with TRAIL1+a-EGFR.

Flow cytometry analysis showed that EGFR was also highly expressed on LS174T colorectal cancer cells (FIG. 11A). After bound to a-EGFR antibody, IgBD-TRAIL01 exerted 10-12 times higher cytotoxicity in LS174T cells (FIG. 11B). The in vivo antitumor effect of IgBD-TRAIL01 bound to a-EGFR (IgBD-TRAIL01+a-EGFR) was evaluated in mice bearing LS174T tumor grafts. PBS and TRAIL01 incubated with the same amount of a-EGFR (TRAIL01+a-EGFR) were used as a control. As shown in FIG. 11C, IgBD-TRAIL01, being able to bind a-EGFR antibody, showed stronger tumor growth suppression. At the end of the observation, the tumor volumes in PBS, TRAIL01+a-EGFR or IgBD-TRAIL01+a-EGFR-treated mice were 1548.3±165.4 mm$^3$, 1055.2±95.7 mm$^3$, and 204±29.7 mm$^3$, respectively. The tumor weights corresponding to these three groups were 0.93±0.1 g, 0.65±0.07 g, and 0.13±0.02 g, respectively (FIG. 10D). Definitely, the tumors in IgBD-TRAIL01+a-EGFR-treated mice were significantly ($p<0.001$) smaller than those in TRAIL01+a-EGFR-treated mice.

Flow cytometry detection also showed that LS174T tumor cells also highly expressed CD47 (FIG. 12A). After incubation with an anti-CD47 antibody (a-CD47, purchased from Bio X Cell Inc.), IgBD-TRAIL01 exerted 6-7 times higher cytotoxicity in LS174T cells (FIG. 12B). In mice bearing LS174T tumor grafts, IgBD-TRAIL01 bound to a-CD47 (IgBD-TRAIL01+a-CD47) showed a stronger inhibitory effect on tumor growth than TRAIL01 incubated with a-CD47 (TRAIL01+ a-CD47). At the end of the observation, the tumor volumes in mice treated with PBS, TRAIL01+a-EGFR or IgBD-TRAIL01+a-EGFR were 1722.4±134.8 mm³, 1109.4±136.6 mm³, and 486.1±74.3 mm³, respectively (FIG. 12C). The corresponding tumor weights of mice in these three group were 1.12±0.05 g, 0.78±0.06 g, and 0.31±0.03 g, respectively (FIG. 12D). The tumors in IgBD-TRAIL01+a-CD47 group were significantly (p<0.001) smaller than those in TRAIL01+a-CD47 group. Above results indicated that fused IgBD could mediate the binding of TRAIL01 to a variety of exogenous antigen-specific IgG antibodies, which enhanced the tumor cell-binding, in vitro cytotoxicity in vivo anti-tumor effect of TRAIL01.

Example 10 Preparation of Fusion Protein IgBD-TRAIL02

According to the molecular design of IgBD-TRAIL in Example 1, the coding genes of IgBD02 and TRAIL01 were ligated to produce a gene encoding the fusion protein IgBD-TRAIL02. The gene was synthesized and cloned into pQE30 plasmid to produce the expression vector pQE30-IgBD-TRAIL02. To induce the expression of the fusion protein, pQE30-IgBD-TRAIL02 plasmid was introduced into *E. coli* M15 cells. The fusion protein IgBD-TRAIL02 was induced and purified according to the method described in Example 1. As shown in FIG. 13, as expected, the molecular weight of IgBD-TRAIL02 was estimated about 28 KD by gel electrophoresis, compared to 20 KD of that of TRAIL01. The prepared IgBD-TRAIL02 protein was visulized as a single band on the gel, indicating that IgBD-TRAIL02 was purified to homogeneity.

```
TRAIL01 nucleotide sequence:
                                        (SEQ ID NO: 9)
5'-gtgagagaaagaggtcctcagagagtagcagctcacataactgggac
cagaggaagaagcaacacattgtcttctccaaactccaagaatgaaaagg
ctctgggccgcaaaataaactcctgggaatcatcaaggagtgggcattca
ttcctgagcaacttgcacttgaggaatggcgaactggtcatccaagaaaa
ggggttttactacatctattcccaaacatactttcgatttcaggaggaaa
taaaagaaaacacaaagaacgacaaacaaatggtccaatatatttacaaa
tacacaagttatcctgaccctatactgctgatgaaaagcgctagaaatag
ttgttggtctaaagatgcagaatacggactctattccatctatcaagggg
gattatttgagataagaaagatgacagaatttttgifictgtaacaaatg
agcacttgatagacatggaccatgaagccagctttttcggggcattttgg
ttggc-3'
```

```
IgBD02 nucleotide sequence:
                                       (SEQ ID NO: 11)
5'-accacctacaagaggtgatcaacggcaagaccagaaaggcgagacca
ccaccaaagcggttgacgcggagaccgcggaaaaggcgttcaaacagtac
gcgaacgacaacggtgtggatggcgtttggacctatgacgatgcgaccaa
gacctttaccgtgaccgaa-3'
```

```
(G45)3 nucleotide sequence:
                                       (SEQ ID NO: 12)
5'-ggeggaggeggttcaggcggaggtggctctggcggtggcggat
ca-3'
```

-continued

```
IgBD-TRAIL02 nucleotide sequence:
                                        (SEQ ID NO: 8)
5'-accacctacaagaggtgatcaacggcaagaccagaaaggcgagacca
ccaccaaagcggttgacgcggagaccgcggaaaaggcgttcaaacagtac
gcgaacgacaacggtgtggatggcgtttggacctatgacgatgcgaccaa
gacctttaccgtgaccgaaggcggaggcggttcaggcggaggtggactgg
cggtggcggatcagtgagagaaagaggtcctcagagagtagcagacacat
aactgggaccagaggaagaagcaacacattgtataccaaactccaagaat
gaaaaggactgggccgcaaaataaactcctgggaatcatcaaggagtggg
cattcattcctgagcaacttgcacttgaggaatggcgaactggtcatcca
agaaaaggggttttactacatctattcccaaacatactttcgatttcagg
aggaaataaaagaaaacacaaagaacgacaaacaaatggtccaatatatt
tacaaatacacaagttatcctgaccctatactgctgatgaaaagcgctag
aaatagttgttggtctaaagatgcagaatacggactctattccatctatc
aagggggattatttgagcttaagaaagatgacagaatttttgifictgta
acaaatgagcacttgatagacatggaccatgaagccagattttcggggca
ttttggttggc-3'
```

```
TRAIL01 amino acid sequence:
                                        (SEQ ID NO: 1)
NH2-VRERGPQRVAAHITGTRGRSNTLSSPNSKNEKALGRKINSWESSRS
GHSFLSNLHLRNGELVIQEKGFYYTYSQTYFRFQEEIKENTKNDKQMVQY
IYKYTSYPDPILLMKSARNSCWSKDAEYGLYSIYQGGLFELKKDDRIFVS
VTNEHLIDMDHEASFFGAFLVG-COOH
```

```
IgBD02 amino acid sequence:
                                        (SEQ ID NO: 3)
NH2-TTYKLVINGKTLKGETTTKAVDAETAEKAFKQYANDNGVDGVWTYD
DATKTFTVTE-COOH
```

```
(G45)3 amino acid sequence:
                                        (SEQ ID NO: 4)
NH2-GGGGSGGGGSGGGGS-COOH
```

```
IgBD-TRAIL02 amino acid sequence:
                                        (SEQ ID NO: 6)
NH2-TTYKLVINGKTLKGETTTKAVDAETAEKAFKQYANDNGVDGVWTYD
DATKTFTVTEGGGGSGGGGSGGGGSVRERGPQRVAAHITGTRGRSNTLSS
PNSKNEKALGRKINSWESSRSGHSFLSNLHLRNGELVIQEKGFYYTYSQT
YFRFQEEIKENTKNDKQMVQYIYKYTSYPDPILLMKSARNSCWSKDAEYG
LYSIYQGGLFELKKDDRIFVSVTNEHLIDMDHEASFFGAFLVG-COOH
```

Example 11 Binding of Fusion Protein IgBD-TRAIL02 to IgG

According to Example 2, the binding of IgBD-TRAIL02 to IgG was analyzed by the size exclusion chromatography. Firstly, IgBD-TRAIL02 were incubated with hIgG at a molar ratio of 1:1 for 30 min at room temperature followed by separation on a gel filtration column Superdex 200 10/30 pre-equilibrated with PBS. Individual IgBD-TRAIL02 and hIgG were used as controls to judge whether any complex with larger molecular weights appeared. As shown in FIG. 14, when IgBD-TRAIL02 and hIgG were incubated together, a single protein peak with retention volume that is smaller than that of individual hIgG and IgBD-TRAIL02 was observed, indicating that IgBD-TRAIL02 and hIgG formed a complex with larger molecular weight after co-incubation. These results demonstrated that IgBD-TRAIL02 could bind to hIgG, indicating that fusing of IgBD02 to the N-terminus of TRAIL-01 could also endow TRAIL01 with IgG-binding ability.

Example 12 Binding of Fusion Protein IgBD-TRAIL02 to Death Receptors and its Cytotoxicity in Tumor Cells According to the method described in Example 3, the binding ability of IgBD-TRAIL02 to death receptor DR4 and DR5 were tested. As shown in FIG. 15A, the affinity of IgBD-TRAIL02 for DR4 and DR5 were 3.96 nM and 1.79 nM, respectively, which were similar to the affinity of TRAIL01 for death receptors, indicating that IgBD-TRAIL02 could bind to death receptors and had the equivalent binding ability to TRAIL01. These results indicated that fusion of IgBD02 to the N-terminus of TRAIL01 did not interfere with the binding of TRAIL01 to the death receptors.

According to the method described in Example 4, the cytotoxicity of IgBD-TRAIL02 in LS174T and HCT116 tumor cells were detected. As shown in FIG. 15B, the killing curves of IgBD-TRAIL02 and TRAIL01 against both tumor cells were nearly identical, indicating that fusion with IgBD02 did not reduce the cytotoxicity of TRAIL01 in tumor cells.

Example 13 Binding to Endogenous IgG Extends the Half-Life of Fusion Protein IgBD-TRAIL02

According to the method described in Example 5, the half-life of IgBD-TRAIL02 was determined after binding to endogenous IgG. As shown in FIGS. 16A and 16B, after $I^{131}$-labeled TRAIL01 and IgBD-TRAIL02 were injected into mice by tail vein, time-dependent decrease was observed in residual radiation and cytotoxicity of residual protein in the blood, but the blood clearance of TRAIL01 was significantly faster than that of IgBD-TRAIL02. The half-life of TRAIL01 was only about 15 min, compared to 14 h of the half-life of IgBD-TRAIL02. These results indicated that IgBD-TRAIL02 could bind to endogenous IgG in blood, which further prolonged the half-life of TRAIL01 by over 50 times.

Example 14 Binding to Endogenous IgG Improves the In Vivo Antitumor Effect of Fusion Protein IgBD-TRAIL02

According to the method in Example 7, the in vivo anti-tumor effects of IgBD-TRAIL02 and TRAIL01 were compared. In mice bearing LS174T tumor grafts, 10 mg/kg TRAIL01 or IgBD-TRAIL02 was injected through the tail vein followed by measuring the tumor size every day. As shown in FIG. 17, the growth suppression of fusion protein IgBD-TRAIL02 on LS174T tumors was significantly stronger than that did by TRAIL01. At the end of observation, the average tumor volumes in PBS-, TRAIL01-, and IgBD-TRAIL02-treated mice were 670±166 mm$^3$, 415±81 mm$^3$ and 97±26 mm$^3$, respectively. Accordingly, the average tumor weights of these three groups were 0.54±0.11 g, 0.27±0.09 g, and 0.07±0.06 g, respectively. These results indicated that the anti-tumor effect of IgBD-TRAIL02 was significantly better than that of TRAIL01.

Examples 1-14 indicated that the IgBD-fusion TRAIL prepared by the present invention showed extremely strong anti-tumor effects, which was significantly greater than that of TRAIL protein as a monotherapy. In addition, the IgBD-fusion TRAIL protein prepared by the present invention could also be used in combination with IgG-type antitumor drugs. Owing to their synergistic antitumor effects, only a small amount of IgBD-fusion TRAIL protein was required to improve the efficacy of IgG-type anti-tumor drugs.

Example 15 Preparation of Fusion Protein IgBD-TRAIL03

According to the molecular design of IgBD-TRAIL in Example 1, the coding genes of IgBD01 and TRAIL02 were ligated to produce the gene encoding fusion protein IgBD-TRAIL03. The gene was synthesized and cloned into pQE30 plasmid. The expression plasmid was designated as pQE30-IgBD-TRAIL03.

According to the conventional molecular biology methods, pQE30-IgBD-TRAIL02 plasmid was introduced into *E. coli* M15. As shown in FIG. 18, the fusion protein IgBD-TRAIL02 was induced and purified to homogeneity according to the method described in Example 1 (FIG. 18).

TRAIL02 nucleotide sequence:
(SEQ ID NO: 13)
5'-gtgagagaaagaggtcctcagagagtagcagctcacataactgggac cagaggaagaagcaacacattgtcttctccaaactccaagaatgaaaagg ctctgggccgcaaaataaactcctgggaatcatcaaggagtgggcattca ttcctgagcaacttgcacttgaggaatggtgaactggtcatccatgatta aagggttttactacatctattcccaaacatactttcgatttcaggaggaa ataaaagaaaacacaaagaacgacaaacaaatggtccaatatatttacaa atacacaagttatcctgacccctatattgttgatgaaaagtgctagaaata gttgttggtctaaagatgcagaatatggactctattccatctatcaaggg ggaatatttgagcttaaggaaaatgacagaatttttgtitctgtaacaaa tgagcacttgaiagacatggaccatgaagccagttttttcggggcctttt tagttggc-3'

TRAIL02 amino acid sequence:
(SEQ ID NO: 14)
NH2-VRERGPQRVAAHITGTRGRSNTLSSPNSKNEKALGRKINSWESSRS

GHSFLSNLHLRNGELVIHEKGFYYIYSQTYFRFQEEIKENTKNDKQMVQY

IYKYTSYPDPILLMKSARNSCWSKDAEYGLYSIYQGGIFELKENDRIFVS

VTNEHLIDMDHEASFFGAPLVG-COOH

IgBD-TRAIL03 nucleotide sequence:
(SEQ ID NO: 15)
accacctacaagctggtgatcaacggcaagaccctgaaaggcgagaccac caccaaagcggttgacgcggagaccgcggcggcggcgttcgcgcagtacg cgcgtcgcaacggtgtggatggcgtttggacctatgacgatgcgaccaag acctttaccgtgaccgaaggcggaggcggttcaggcggaggtggctctgg cggtggcggatcagtgagagaaagaggtcctcagagagtagcagctcaca taactgggaccagaggaagaagcaacacattgtcttctccaaactccaag aatgaaaaggctctgggccgcaaaataaactcctgggaatcatcaaggag -continued
tgggcattcattcctgagcaacttgcacttgaggaatggtgaactggtca tccatgaaaagggtntactacatctattcccaaacatactttcgatttc aggaggaaataaaagaaaacacaaagaacgacaaacaaatggtccaatat autacaaatacacaagttatcctgaccctatattgttgatgaaaagtgct agaaatagttgttggtctaaagatgcagaatatggactctattccatcta tcaaggggaatatttgagcttaaggaaaatgacagaattttgtttctg taacaaatgagcacttgatagacatggaccatgaagccagttttttcggg gccttttttagttggc-3'

IgBD-TRAIL03 amino acid sequence:
(SEQ ID NO: 16)
NH2-TTYKLVINGKTLKGETTTKAVDAETAAAAFAQYARRNGVDGVWTYD

DATKTFTVTEGGGGSGGGGSGGGGSVRERGPQRVAAHITGTRGRSNTLSS

PNSKNEKALGRKINSWESSRSGHSFLSNLHLRNGELVIHEKGFYYIYSQT

YFRFQEEIKENTKNDKQMVQYIYKYTSYPDPILLMKSARNSCWSKDAEYG

LYSIYQGGIFELKENDRIFVSVTNEHLIDMDHEASFFGAFLVG-COOH

Example 16 Fusion Protein ABD-TRAIL01 Did not Show Obviously Improved Anti-Tumor Effect Both albumin and IgG in plasma were long-acting proteins with similar half-lives. In order to prove whether the improvement of the in vivo anti-tumor effect of IgBD-TRAIL was only dependent on the prolongation of half-life, the present invention decided to fuse an albumin-binding domain (ABD) to TRAIL01 to produce ABD-TRAIL01. ABD was derived from Streptococcus Protein G and had a high affinity for albumin (Jonsson et al., Protein Eng. Des. Sel. 2008, 21: 515-527). According to the molecular design of IgBD-TRAIL01, ABD was genetically fused to the N-terminus of TRAIL01 to 25 produce ABD-TRAIL01. The fusion protein was prepared according to the method described in Example 1. As shown in FIG. 19A, purified protein was visualized as single band on SDS-PAGE gel, indicating that ABD-TRAIL01 was purified to homogeneity. The cytotoxicity assay showed that, compared with TRAIL01, ABD-TRAIL01 showed significantly prolonged half-life (FIG. 19B) that is similar to the half-life of IgBD-TRAIL (FIG. 5B), indicating that the binding of ABD-TRAIL01 to endogenous albumin significantly extended the half-life of TRAIL01. However, the antitumor effect of 5 mg/kg, ABD-TRAIL01 (FIG. 19C, D) in mice bearing COLO205 tumor grafts was significantly weaker than that of 0.5 mg/kg IgBD-TRAIL01 (FIG. 5A). These results suggested that the improvement of the anti-tumor effect of IgBD-TRAIL01 was attributed not only to the extended half-life of TRAIL01.

ABD nucleic acid sequence:
(SEQ ID NO: 17)
5-ctggctgaagcaaaagtcctggcgaatcgtgaactggataagtatggc gtctcggatttctacaagcgtctgatcaataaagcaaaaaccgtggaagg cgttgaagcactgaaactgcatattctggccgcactgccg-3

ABD amino acid sequence:
(SEQ ID NO: 18)
NH2-LAEAKVLANRELDKYGVSDFYKRLINKAKTVEGVEALKLHILAAL

P-COOH

ABD-TRAIL01 nucleic acid sequence:
(SEQ ID NO: 19)
5-ctggctgaagcaaaagtcaggcgaatcgtgaactggataagtatggcg tctcggatttctacaagcgtctgatcaataaagcaaaaaccgtggaaggc gttgaagcactgaaactgcatattctggccgcactgccgggcggaggcgg ttcaggcggaggtggctctggcggtggcggatcagtgagagaaagaggtc ctcagagagtagcagctcacataactgggaccagaggaagaagcaacaca ttgtatctccaaactccaagaatgaaaaggctctgggccgcaaaataaac tcctgggaatcatcaaggagtgggcattcattcctgagcaacttgcactt gaggaatggcgaactggtcatccaagaaaaggggttttactacatctatt cccaaacatactttcgatttcaggaggaaataaaagaaaacacaaagaac gacaaacaaatggtccaatatatttacaaatacacaagttatcctgaccc tatactgctgatgaaaagcgctagaaatagttgttggtctaaagatgcag aatacggactctattccatctatcaaggggggattatttgagataagaaag atgacagaattttttgtttctgtaacaaatgagcacttgatagacatggac catgaagccagattttcggggcctttttggttggc-3

ABD-TRAIL01 amino acid sequence:
(SEQ ID NO: 20)
NH2-LAEAKVLANRELDKYGVSDFYKRLINKAKTVEGVEALKLHILAALP

GGGGSGGGGSGGGGSVRERGPQRVAAHITGTRGRSNTLSSPNSKNEKALG

RKINSWESSRSGHSFLSNLHLRNGELVIQEKGFYYTYSQTYFRFQEEIKE

NTKNDKQMVQYIYKYTSYPDPILLMKSARNSCWSKDAEYGLYSIYQGGLF

ELKKDDRIFVSVTNEHLIDMDHEASFFGAFLVG-COOH

Example 17 the Fusion Protein IgBD-IL2 Doesn't Show Obvious IgG-Binding Ability To verify that IgBD fusion may not endow any protein with IgG-binding ability, the present invention further designed to fuse IgBD01 to the N-terminus of IL2 to produce IgBD-IL2 according to the molecular design of IgBD-TRAIL01. The IgBD-IL2 fusion protein was prepared using methods described in Example 1. As shown in FIG. 20A, the purified protein visualized as a single band on SDS-PAGE gel, indicating that IgBD-IL2 was purified to homogeneity. The IgG-binding of IgBD-IL2 and IgBD-TRAIL01 was compared using ELISA according to Example 2. It was found that IgBD-TRAIL01, but not IgBD-IL2, showed obvious IgG-binding (FIG. 20B). Gel filtration further revealed that the mixture of IgBD-IL2 and IgG was separated as two protein peaks corresponding to IgG and IgBD-IL2, indicating that IgBD-IL2 did not bind IgG (FIG. 20C). Under the same conditions, IgBD-TRAIL01 and IgG form a protein complex with a larger molecular weight than IgG after co-incubation, indicating that IgBD-TRAIL01 bound IgG (FIG. 2B). These results suggested that IgBD domain in IgBD-IL2 might lose its IgG binding ability due to intermolecular interaction.

IL2 nucleic acid sequence:
(SEQ ID NO: 21)
5-gcacctacttcaagttctacaaagaaaacacagctacaactggagcat
ttactgctggatttacagatgattttgaatggaattaataattacaagaa
tcccaaactcaccaggatgctcacatttaagttttacatgcccaagaagg
ccacagaactgaaacatcttcagtgtctagaagaagaactcaaacctctg
gaggaagtgctaaatttagctcaaagcaaaaactttcacttaagacccag
ggacttaatcagcaatatcaacgtaatagttctggaactaaagggatctg
aaacaacartcatgtgtgaatatgctgatgagacagcaaccattgtagaa
tttctgaacagatggattacctttgtcaaagcatcatctcaacactgac
t-3

IL2 amino acid sequence:
(SEQ ID NO: 22)
NH2-APTSSSTKKTQLQLEHLLLDLQMILNGINNYKNPKLTRMLTFKFYM
PKKATELKHLQCLEEELKPLEEVLNLAQSKNFHLRPRDLISNINVIVLEL
KGSETTFMCEYADETATIVEFLNRVVITFCQSIISTLT-COOH IgBD-IL2 nucleic acid sequence:
(SEQ ID NO: 23)
5-accacctacaagctggtgatcaacggcaagaccctgaaaggcgagacc
accaccaaagcggttgacgcggagaccgcggcggcggcgttcgcgcagta
cgcgcgtcgcaacggtgtggatggcgtttggacctatgacgatgcgacca
gacctttaccgtgaccgaaggcggaggcggttcaggcggaggtggctct
ggcggtggcggatcagcacctacttcaagttctacaaagaaaacacagct
acaactggagcatttactgctggatttacagatgattttgaatggaatta
ataattacaagaatcccaaactcaccaggatgctcacatttaagttttac
atgcccaagaaggccacagaactgaaacatcttcagtgtctagaagaaga
actcaaacctctggaggaagtgctaaatttagctcaaagcaaaaactttc
acttaagacccagggacttaatcagcaatatcaacgtaatagttctggaa
ctaaagggatctgaaacaacattcatgtgtgaatatgctgatgagacagc
aaccattgtagaatttctgaacagatggataccttttgtcaaagcatcat
ctcaacactgact-3'

IgBD-IL2 amino acid sequence:
(SEQ ID NO: 24)
NH2-TTYKLVINGKTLKGETTTKAVDAETAAAAFAQYARRNGVDGVWTYD
DATKTFTVTEGGGGSGGGGSGGGGSAPTSSSTKKTQLQLEHLLLDLQMIL
NGINNYKNPKLTRMLTFKFYMPKKATELKHLQCLEEELKPLEEVLNLAQS
KNFHLRPRDLISNINVIVLELKGSETTFMCEYADETATIVEFLNRWITFC
QSIISTLT-COOH

Example 18 the Fusion Protein F3-TRAIL Containing IgG Binding Domain Fc3 and TRAIL01 could not be Expressed in E. coli In order to determine whether any IgG binding domain could be fused to TRAIL01 to produce IgG-binding, we selected the Fc3 peptide that also had IgG binding ability (Science, 2000, 287, 1279-1283) to produce fusion protein with TRAIL. According to IgBD-TRAIL01 molecular construction method described in Example 1, Fc3 was linked to the N-terminus of TRAIL01, and F3-TRAIL01 was designed, and the same vector and bacteria were used for expression. Comparing the total bacterial proteins before and after induction, it was found that large amount of IgBD-TRAIL01 could be produced in E. coli, whereas little Fc3-TRAIL01 was expressed under the same conditions (FIG. 21). These results indicated that IgBD provided by this invention, but not any IgG-binding domain, could be used to prepare IgBD-TRAIL fusion protein that was highly expressed in E. coli.

Fc3 nucleic acid sequence:
5'-gactgtgcgtggcacctgggagaattggtgtggtgtaca-3'

Fc3 amino acid sequence:
NH2-DCAWHLGELVWCT-COOH

Fc3-TRAIL01 nucleic acid sequence:
5'-gactgtgcgtggcacctgggagaattggtgtggtgtacaggcggagg
cggttcaggcggaggtggctctggcggtggcggatcagtgagagaaagag
gtcctcagagagtagcagctcacataactgggaccagaggaagaagcaac
acattgtcttctccaaactccaagaatgaaaaggctctgggccgcaaaat
aaactcctgggaatcatcaaggagtgggcattcattcctgagcaacttgc
acttgaggaatggcgaactggtcatccaagaaaaggggttttactactc
tattcccaaacatactttcgatttcaggaggaaataaaagaaaacacaaa
gaacgacaaacaaatggtccaatatatttacaaatacacaagttatcctg
accctatactgctgatgaaaagcgctagaaatagttgttggtctaaagat
gcagaatacggactctattccatctatcaaggggattatttgagcttaa
gaaagatgacagaattttttgtttctgtaacaaatgagcacttgatagaca
tggaccatgaagccagcttttcggggccttttggttggc-3'

Fc3-TRAIL01 amino acid sequence:
NH2-DCAWHLGELVWCTGGGGSGGGGSGGGGSVRERGPQRVAAHITGTRG
RSNTLSSPNSKNEKALGRKINSWESSRSGHSFLSNLHLRNGELVIQEKGF
YYIYSQTYFRFQEEIKENTKNDKQMVQYIYKYTSYPDPILLMKSARNSCW
SKDAEYGLYSIYQGGLFELKKDDRIFVSVTNEHLIDMDHEASFFGAFL
VG-COOH TRAIL is cytotoxic to tumor cells. IgBD fusion might extend the half-life of TRAIL. However, on the one hand, examples 16, 17 and 18 indicated that the fusion protein IgBD-TRAIL produced by the present invention exerted significantly increased antitumor effect by relying on the simple combination of TRAIL and IgBD to prolong the half-life of TRAIL. On the other hand, IgBD fusion to TRAIL, but not any other protein could exert IgG-binding ability. In addition, the fusion protein containing TRAIL fused to IgBD, but not any other IgG-binding domain, could be highly expressed in E. coli. In the IgBD-TRAIL fusion protein produced by the present invention, TRAIL and IgBD could support each other in function to achieve unexpected anti-cancer effects.

The invention claimed is:

1. A nucleotide sequence, comprising:
   (1) a sequence segment encoding a function domain of TRAIL; and
   (2) a sequence segment encoding a IgG-binding domain;
   wherein the TRAIL is derived from monkey or human TRAIL the IgG-binding domain is from *streptococcus* protein G, and
   wherein the nucleotide sequence is shown as any one of SEQ ID NO:7, 8 or 15.

2. The nucleotide sequence according to claim 1, wherein the sequence segment encoding the functional domain of TRAIL is shown in SEQ ID NO:9 or 13.

3. The nucleotide sequence according to claim 1, wherein the sequence segment encoding of the IgG-binding domain is shown in SEQ ID NO:10 or 11.

4. A recombinant vector containing the nucleotide sequence of claim 1.

5. The recombinant vector according to claim 4, wherein the recombinant vector is a recombinant plasmid or a genetic engineering vector.

6. A recombinant expression host cell containing the recombinant vector of claim 4.

7. The recombinant expression host cell according to claim 6, wherein said recombinant expression host cell is *Escherichia coli*.

8. A fusion protein encoded by the nucleotide sequence according to claim 1.

9. An anti-tumor drug, comprising the fusion protein according to claim 8 as an active component, and pharmaceutically acceptable excipients.

10. The anti-tumor drug according to claim 9, further comprising antibodies of immunoglobulin G.

11. The anti-tumor drug according to claim 10, wherein said antibodies of immunoglobulin G comprise antibodies against EGFR, CD47, CD20, HER2, VEGF, PD-L1, PD1, or CTLA4.

12. An anti-tumor drug combination, comprising the anti-tumor drug according to claim 10, other classes of anti-tumor drugs, and pharmaceutically acceptable carriers.

13. The drug combination according to claim 12, wherein said antibodies of immunoglobulin G comprise antibodies against EGFR, CD47, CD20, HER2, VEGF, PD-L1, PD1, or CTLA4.

14. A method for treatment of tumor, comprising administering an effective amount of a composition comprising the fusion protein according to claim 8 to a subject in need thereof.

15. The method according to claim 14, wherein the treatment of tumors comprises treating colon cancer, rectal adenocarcinoma, breast cancer, lung cancer, or liver cancer.

* * * * *